US011473111B2

(12) United States Patent
Lee et al.

(10) Patent No.: US 11,473,111 B2
(45) Date of Patent: Oct. 18, 2022

(54) **RECOMBINANT *CORYNEBACTERIUM* HAVING 1,3-PDO PRODUCTIVITY AND REDUCED 3-HP PRODUCTIVITY, AND METHOD FOR PRODUCING 1,3-PDO BY USING SAME**

(71) Applicants: KOREA ADVANCED INSTITUTE OF SCIENCE AND TECHNOLOGY, Daejeon (KR); HANWHA SOLUTIONS CORPORATION, Seoul (KR)

(72) Inventors: Sang Yup Lee, Daejeon (KR); Jae Sung Cho, Daejeon (KR); Je Woong Kim, Daejeon (KR); Cindy Pricilia Surya Prabowo, Daejeon (KR); Taehee Han, Daejeon (KR); Yoo Sung Ko, Daejeon (KR)

(73) Assignees: KOREA ADVANCED INSTITUTE OF SCIENCE AND TECHNOLOGY, Daejeon (KR); HANWHA SOLUTIONS CORPORATION, Seoul (KR)

( * ) Notice: Subject to any disclaimer, the term of this patent is extended or adjusted under 35 U.S.C. 154(b) by 31 days.

(21) Appl. No.: 17/055,971

(22) PCT Filed: Apr. 24, 2019

(86) PCT No.: PCT/KR2019/004961
§ 371 (c)(1),
(2) Date: Nov. 16, 2020

(87) PCT Pub. No.: WO2019/225865
PCT Pub. Date: Nov. 28, 2019

(65) Prior Publication Data
US 2021/0214753 A1    Jul. 15, 2021

(30) Foreign Application Priority Data

May 24, 2018 (KR) ........................ 10-2018-0058952

(51) Int. Cl.
| | | |
|---|---|---|
| *C12P 7/18* | (2006.01) | |
| *C12N 15/77* | (2006.01) | |
| *C07K 14/34* | (2006.01) | |
| *C12N 15/67* | (2006.01) | |

(52) U.S. Cl.
CPC .............. *C12P 7/18* (2013.01); *C07K 14/34* (2013.01); *C12N 15/67* (2013.01); *C12N 15/77* (2013.01); *C12Y 101/01006* (2013.01); *C12Y 101/01202* (2013.01); *C12Y 102/01003* (2013.01); *C12Y 207/0103* (2013.01)

(58) Field of Classification Search
CPC ......... C12P 7/18; C07K 14/34; C07K 14/245; C12N 15/67; C12N 15/77; C12N 9/0006; C12N 9/0008; C12N 9/1205; C12N 15/52; C12Y 101/01006; C12Y 101/01202; C12Y 102/01003; C12Y 207/0103; C12Y 402/0103
See application file for complete search history.

(56) References Cited

U.S. PATENT DOCUMENTS

| 6,514,733 B1 | 2/2003 | Emptage et al. |
|---|---|---|
| 8,236,994 B2 | 8/2012 | Soucaille |

FOREIGN PATENT DOCUMENTS

| CN | 105400831 A | 3/2016 |
|---|---|---|
| EP | 3741860 A1 | 11/2020 |
| KR | 1020090120083 A | 11/2009 |
| KR | 1020120099315 A | 9/2012 |
| KR | 1020130022691 A | 3/2013 |
| KR | 1020180111680 A | 10/2018 |
| WO | 2008091093 A1 | 7/2008 |

OTHER PUBLICATIONS

Sousa et al., Microbiology 148(Pt5):1291-1303, 2002.*
Witkowski et al., Biochemistry 38:11643-11650, 1999.*
Tang et al., Phil Trans R Soc B 368:Mar. 18, 2012, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Zhou et al., Cell Mol Life Sci 63(19-20):2260-2290, 2006.*
Kozak, M., Gene 234:187-208, 1999.*
Li et al., Metabolic Engineering 70:79-88, 2022.*
Rittman et al., Applied and Environmental Microbiology 74(20):6216-6222, 2008.*
Chen, Z., et al., "Metabolic Engineering of Corynebacterium Glutamicum for the Production of 3-hydroxypropionic Acid from Glucose and Xylose", "Metabolic Engineering", Jan. 2017, pp. 151-158, vol. 39.
Cho, J.S., et al., "CRISPR/Cas9-Coupled Recombineering for Metabolic Engineering of Corynebacterium Glutamicum", "Metab. Eng", 2017, pp. 1-39.
Eikmanns, B. J., et al., "A family of Corynebacterium glutamicum/ *Escherichia coli* shuttle vectors for cloning, controlled gene expression, and promoter probing", "Gene", 1991, pp. 93-98, vol. 102.
Huang, J., et al., "Cofactor Recycling for Co-Production of 1,3-propanediol and Glutamate by Metabolically Engineered Corynebacterium Glutamicum", "Nature/ Scientific Reports", 2017, pp. 1-10.

(Continued)

*Primary Examiner* — Delia M Ramirez
(74) *Attorney, Agent, or Firm* — Hultquist, PLLC; Steven J. Hultquist

(57) ABSTRACT

The present invention relates to recombinant *Corynebacterium* having 1,3-PDO productivity and reduced 3-HP productivity, and a method for producing 1,3-PDO by using same. When a *Corynebacterium glutamicum* variant according to the present invention is used, the productivity of 3-HP, which is a by-product, is inhibited by using low-cost glycerol as a carbon source, and thus 1,3-PDO can be produced with high efficiency.

3 Claims, 6 Drawing Sheets

Specification includes a Sequence Listing.

(56) References Cited

OTHER PUBLICATIONS

Ko, Y., et al., "Deletion of Putative Oxidoreductases from Klebsiella Pneumoniae J2B Could Reduce 1,3-propanediol During the Production of 3-hydroxypropionic Acid from Glycerol", "Biotechnology and Bioprocess Engineering", 2015, pp. 834-843, vol. 20.
Lee, C.S., et al., "A Review: Conversion of Bioglycerol into 1,3-propanediol via Biological and Chemical Method", "Renewable and Sustainable Energy Reviews", 2015, pp. 963-972, vol. 42.
Neumann, E., et al., "Gene Transfer into Mouse Lyoma Cells by Electroporation in High Electric Fields", "The EMBO Journal", Jun. 30, 1982, pp. 841-845, vol. 1, No. 7.
Yim, S.S., et al., "Isolation of Fully Synthetic Promoters for High-Level Gene Expression in Corynebacterium Glutamicum", "Biotechnology and Bioengineering", 2013, pp. 1-37.
Rittmann, D., et al., "Engineering of a Glycerol Utilization Pathway for Amino Acid Production by Corynebacterium glutamicum", Applied and Environmental Microbiology, 2008, pp. 6216-6222, vol. 74, No. 20, Publisher: American Society for Microbiology.
Bong, H-J., et al., "Tripartite Regulation of the glpFKD Operon Involved in Glycerol Catabolism by GylR, Crp, and SigF in *Mycobacterium smegmatis*", Journal of Bacteriology, 2019, p. 201:e00511-19. https://https://doi.org/10.1128/JB.00511-19, vol. 201, No. 24, Publisher: American Society for Microbiology.
Chen, L., et al., "Exploring Lactobacillus reuteri DSM20016 as a biocatalyst for transformation of longer chain 1,2-diols-Limits with microcompartment", Plos One, 2017, Page(s) https://doi.org/10.1371/journal.pone.0185734, vol. 12, No. 9.

\* cited by examiner

[Fig. 1]
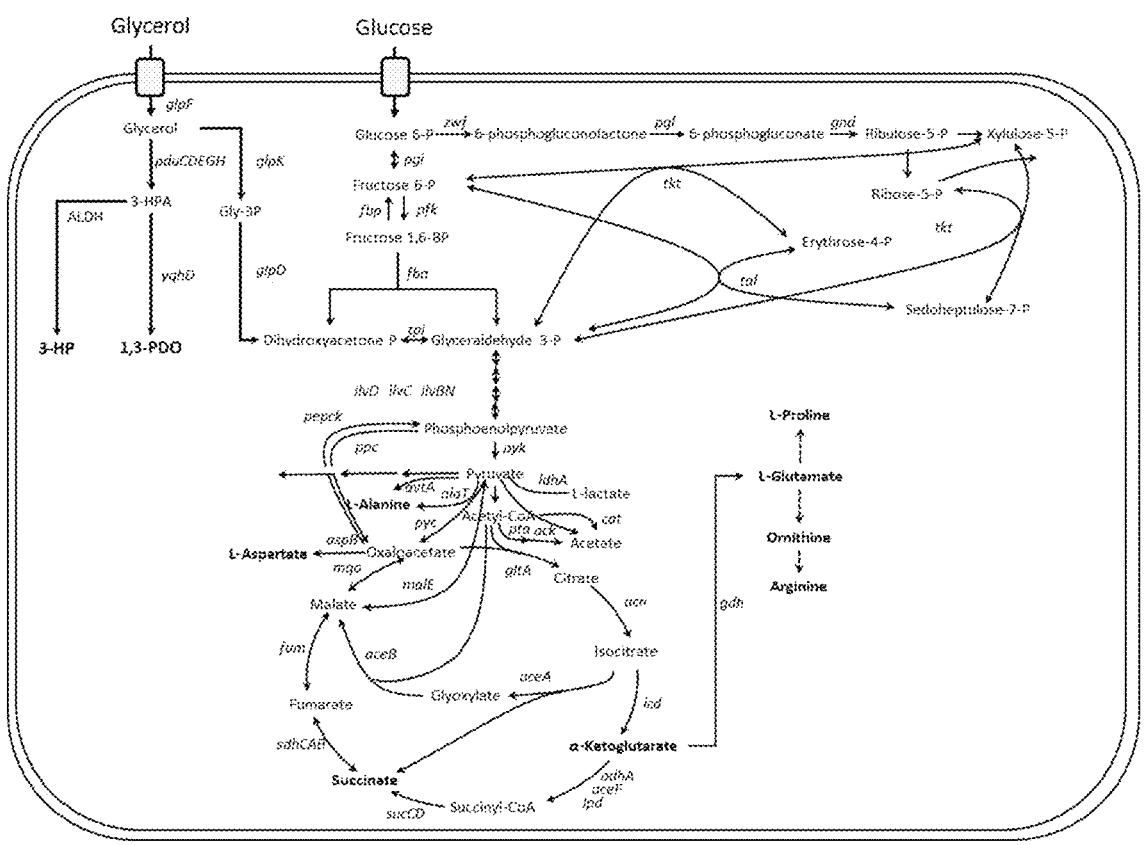

[Fig. 2]
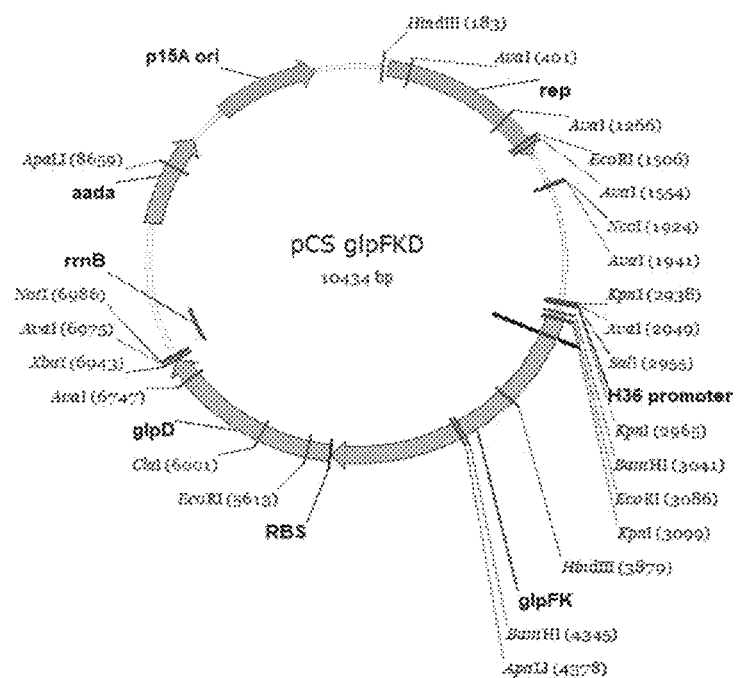

[Fig. 3]
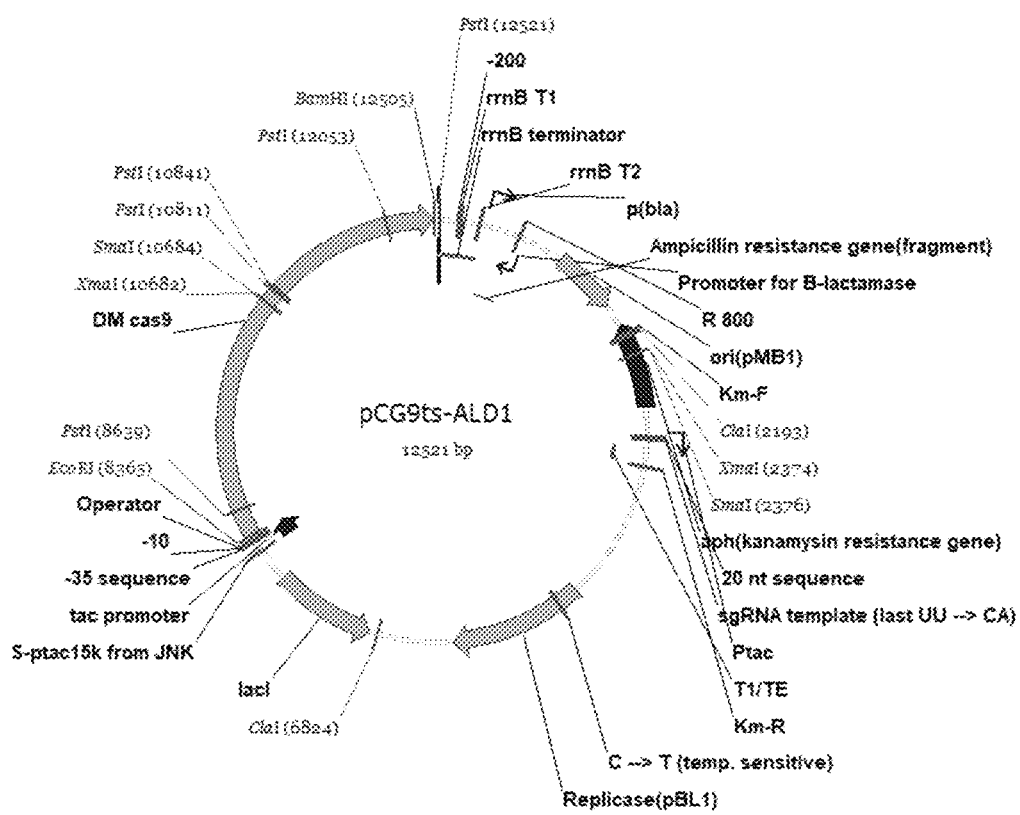

[Fig. 4]
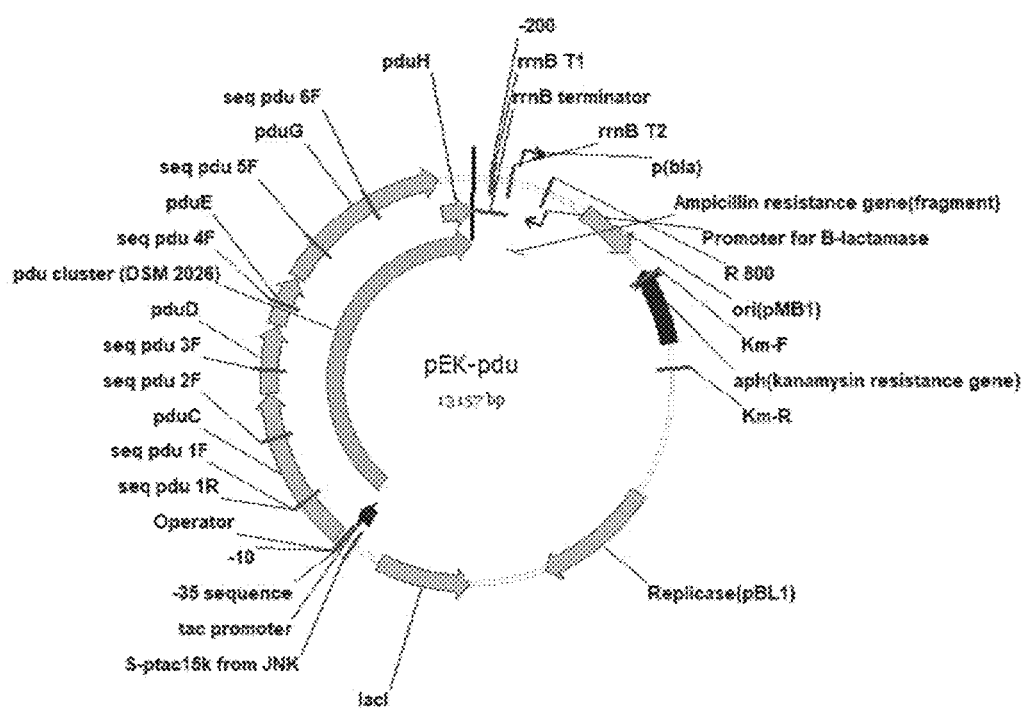

[Fig. 5]
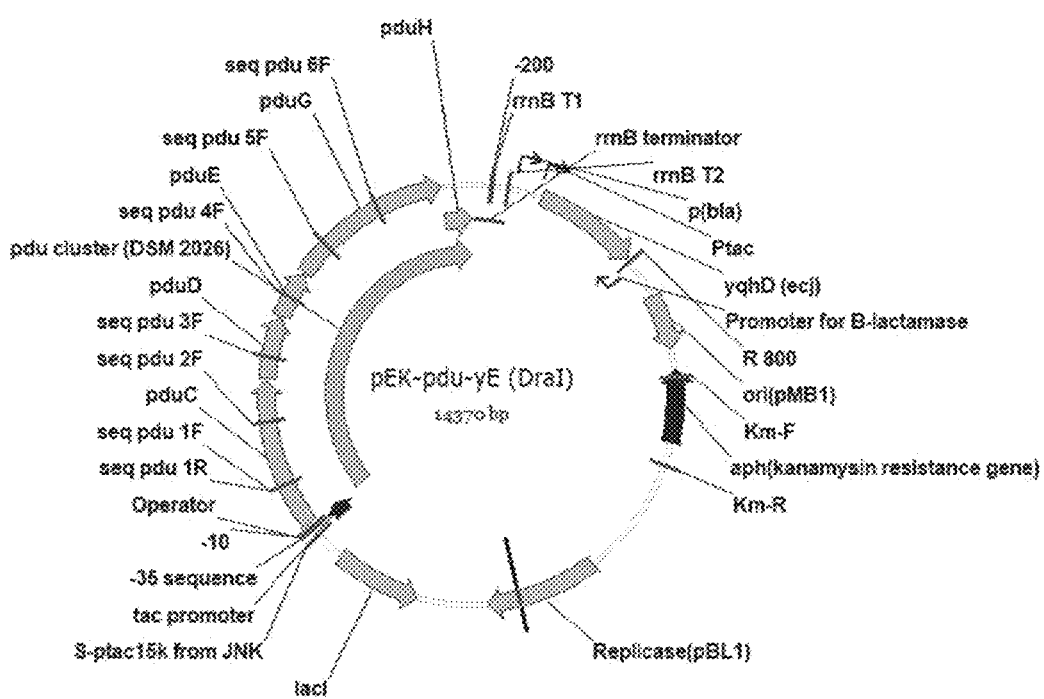

[Fig. 6]
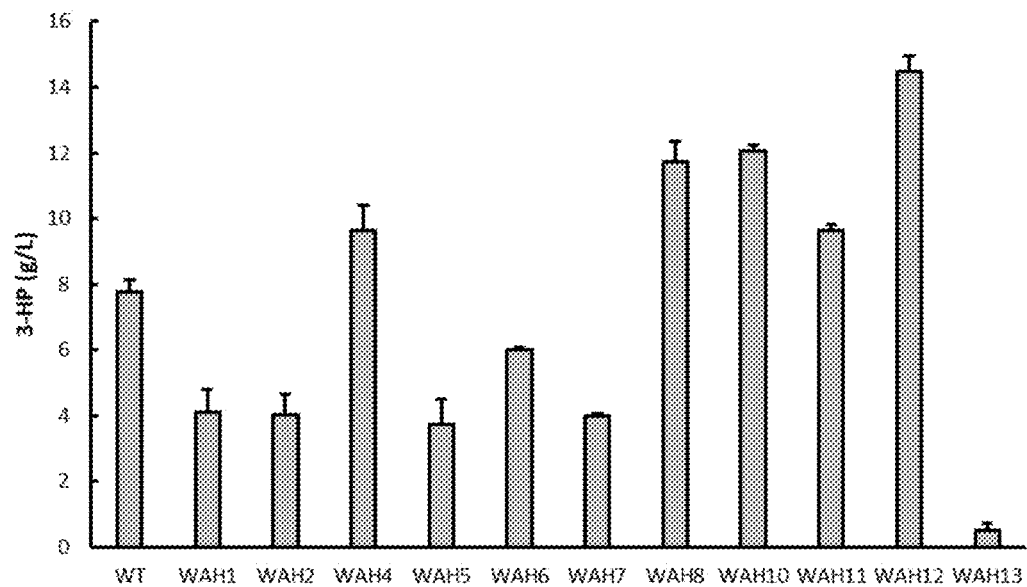
[Fig. 7]
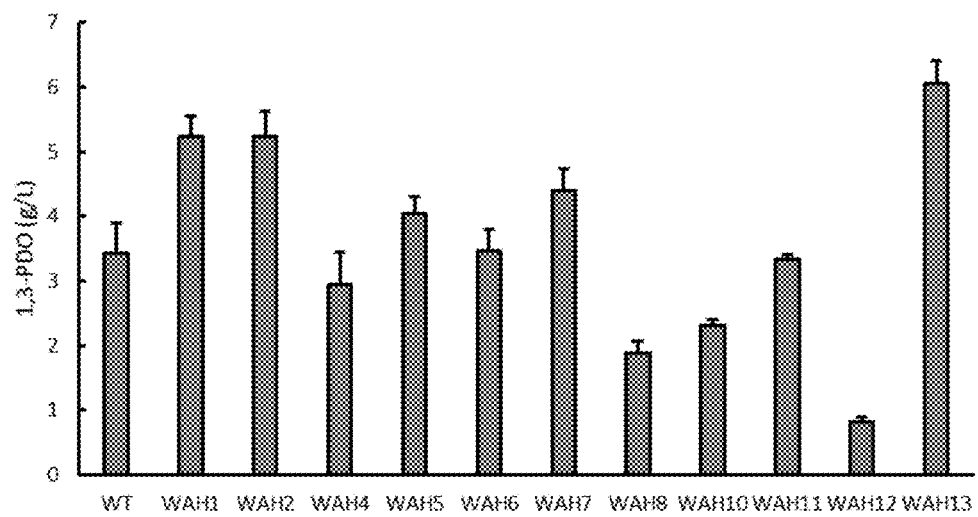

SEQUENCE LISTING

```
<160> NUMBER OF SEQ ID NOS: 68

<210> SEQ ID NO 1
<211> LENGTH: 47
<212> TYPE: DNA
<213> ORGANISM: Artificial Sequence
<220> FEATURE:
<223> OTHER INFORMATION: primer

<400> SEQUENCE: 1
ttggttggta ggagtagcat gggatccatg agtcaaacat caacctt            47

<210> SEQ ID NO 2
<211> LENGTH: 40
<212> TYPE: DNA
<213> ORGANISM: Artificial Sequence
<220> FEATURE:
<223> OTHER INFORMATION: primer

<400> SEQUENCE: 2
gtttccatct atatctcctt ttattcgtcg tgttcttccc                     40

<210> SEQ ID NO 3
<211> LENGTH: 32
<212> TYPE: DNA
<213> ORGANISM: Artificial Sequence
<220> FEATURE:
<223> OTHER INFORMATION: primer

<400> SEQUENCE: 3
aaggagatat agatggaaac caaagatctg at                             32

<210> SEQ ID NO 4
<211> LENGTH: 50
<212> TYPE: DNA
<213> ORGANISM: Artificial Sequence
```

```
<220> FEATURE:
<223> OTHER INFORMATION: primer

<400> SEQUENCE: 4
taattataat ggccggctgg gcctctagag ttacgacgcc agcgataacc        50

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
tctagaggcc cagccggcca ttataattag                              30

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
ggatcccatg ctactcctac caaccaaggt                              30

<210> SEQ ID NO 7
<211> LENGTH: 20
<212> TYPE: DNA
<213> ORGANISM: Artificial Sequence
<220> FEATURE:
<223> OTHER INFORMATION: sgRNA

<400> SEQUENCE: 7
ttcgtggact aagaaacggt                                         20

<210> SEQ ID NO 8
<211> LENGTH: 20
<212> TYPE: DNA
<213> ORGANISM: Artificial Sequence
<220> FEATURE:
<223> OTHER INFORMATION: sgRNA

<400> SEQUENCE: 8
tgcaggattg tagacaggag                                         20

<210> SEQ ID NO 9
<211> LENGTH: 20
<212> TYPE: DNA
<213> ORGANISM: Artificial Sequence
<220> FEATURE:
<223> OTHER INFORMATION: sgRNA

<400> SEQUENCE: 9
ttcacctcag agacgattag                                         20

<210> SEQ ID NO 10
<211> LENGTH: 20
<212> TYPE: DNA
<213> ORGANISM: Artificial Sequence
<220> FEATURE:
<223> OTHER INFORMATION: sgRNA

<400> SEQUENCE: 10
tgtttgctaa agagtaggaa                                         20
```

```
<210> SEQ ID NO 11
<211> LENGTH: 20
<212> TYPE: DNA
<213> ORGANISM: Artificial Sequence
<220> FEATURE:
<223> OTHER INFORMATION: sgRNA

<400> SEQUENCE: 11
aactccccgc gaaagatccg                                                    20

<210> SEQ ID NO 12
<211> LENGTH: 20
<212> TYPE: DNA
<213> ORGANISM: Artificial Sequence
<220> FEATURE:
<223> OTHER INFORMATION: sgRNA

<400> SEQUENCE: 12
ttcggagaca cacacatgta                                                    20

<210> SEQ ID NO 13
<211> LENGTH: 20
<212> TYPE: DNA
<213> ORGANISM: Artificial Sequence
<220> FEATURE:
<223> OTHER INFORMATION: sgRNA

<400> SEQUENCE: 13
ccagtgactt tagagctagg                                                    20

<210> SEQ ID NO 14
<211> LENGTH: 20
<212> TYPE: DNA
<213> ORGANISM: Artificial Sequence
<220> FEATURE:
<223> OTHER INFORMATION: sgRNA

<400> SEQUENCE: 14
ccaactgata tcgtgctgta                                                    20

<210> SEQ ID NO 15
<211> LENGTH: 20
<212> TYPE: DNA
<213> ORGANISM: Artificial Sequence
<220> FEATURE:
<223> OTHER INFORMATION: sgRNA

<400> SEQUENCE: 15
gtcgccagtg tatgcgtgaa                                                    20

<210> SEQ ID NO 16
<211> LENGTH: 20
<212> TYPE: DNA
<213> ORGANISM: Artificial Sequence
<220> FEATURE:
<223> OTHER INFORMATION: sgRNA

<400> SEQUENCE: 16
gcgcagcaaa gctacgtttc                                                    20

<210> SEQ ID NO 17
<211> LENGTH: 20
<212> TYPE: DNA
<213> ORGANISM: Artificial Sequence
<220> FEATURE:
<223> OTHER INFORMATION: sgRNA
```

<400> SEQUENCE: 17
atcgtcgtaa ggattgatat                                                20

<210> SEQ ID NO 18
<211> LENGTH: 20
<212> TYPE: DNA
<213> ORGANISM: Artificial Sequence
<220> FEATURE:
<223> OTHER INFORMATION: sgRNA

<400> SEQUENCE: 18
gaggttatag cgccatttac                                                20

<210> SEQ ID NO 19
<211> LENGTH: 20
<212> TYPE: DNA
<213> ORGANISM: Artificial Sequence
<220> FEATURE:
<223> OTHER INFORMATION: sgRNA

<400> SEQUENCE: 19
cttgccaatc cgattagagc                                                20

<210> SEQ ID NO 20
<211> LENGTH: 47
<212> TYPE: DNA
<213> ORGANISM: Artificial Sequence
<220> FEATURE:
<223> OTHER INFORMATION: primer for sgRNA-T1/TE fragment

<400> SEQUENCE: 20
tatagatatc ccgcggtata ttaattaata taaacgcaga aaggccc                  47

<210> SEQ ID NO 21
<211> LENGTH: 51
<212> TYPE: DNA
<213> ORGANISM: Artificial Sequence
<220> FEATURE:
<223> OTHER INFORMATION: primer for sgRNA-T1/TE fragment

<400> SEQUENCE: 21
tggatgatgg ggcgattcag gtatagatat cttgacaatt aatcatcggc t             51

<210> SEQ ID NO 22
<211> LENGTH: 44
<212> TYPE: DNA
<213> ORGANISM: Artificial Sequence
<220> FEATURE:
<223> OTHER INFORMATION: primer for sgRNA-T1/TE fragment

<400> SEQUENCE: 22
aaggtgttgc tgactcatac caggtataga tatcccgcgg tata                     44

<210> SEQ ID NO 23
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 23
ttgacaatta atcatcggct cgtataatgt gtggttcgtg gactaagaaa cggtgtttta    60
gagctagaaa tagcaagt                                                  78

```
<210> SEQ ID NO 24
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 24
ttgacaatta atcatcggct cgtataatgt gtggtgcagg attgtagaca ggaggtttta    60
gagctagaaa tagcaagt                                                  78

<210> SEQ ID NO 25
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 25
ttgacaatta atcatcggct cgtataatgt gtggttcacc tcagagacga ttaggtttta    60
gagctagaaa tagcaagt                                                  78

<210> SEQ ID NO 26
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 26
ttgacaatta atcatcggct cgtataatgt gtggtgtttg ctaaagagta ggaagtttta    60
gagctagaaa tagcaagt                                                  78

<210> SEQ ID NO 27
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 27
ttgacaatta atcatcggct cgtataatgt gtggaactcc ccgcgaaaga tccggtttta    60
gagctagaaa tagcaagt                                                  78

<210> SEQ ID NO 28
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 28
ttgacaatta atcatcggct cgtataatgt gtggttcgga gacacacaca tgtagtttta    60
gagctagaaa tagcaagt                                                  78

<210> SEQ ID NO 29
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 29
```

```
ttgacaatta atcatcggct cgtataatgt gtggccagtg actttagagc tagggtttta      60
gagctagaaa tagcaagt                                                    78
```

<210> SEQ ID NO 30
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 30

```
ttgacaatta atcatcggct cgtataatgt gtggccaact gatatcgtgc tgtagtttta      60
gagctagaaa tagcaagt                                                    78
```

<210> SEQ ID NO 31
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 31

```
ttgacaatta atcatcggct cgtataatgt gtgggtcgcc agtgtatgcg tgaagtttta      60
gagctagaaa tagcaagt                                                    78
```

<210> SEQ ID NO 32
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 32

```
ttgacaatta atcatcggct cgtataatgt gtgggcgcag caaagctacg tttcgtttta      60
gagctagaaa tagcaagt                                                    78
```

<210> SEQ ID NO 33
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 33

```
ttgacaatta atcatcggct cgtataatgt gtggatcgtc gtaaggattg atatgtttta      60
gagctagaaa tagcaagt                                                    78
```

<210> SEQ ID NO 34
<211> LENGTH: 78
<212> TYPE: DNA
<213> ORGANISM: Artificial Sequence
<220> FEATURE:
<223> OTHER INFORMATION: primer for pCG9ts-series vector preparation

<400> SEQUENCE: 34

```
ttgacaatta atcatcggct cgtataatgt gtgggaggtt atagcgccat ttacgtttta      60
gagctagaaa tagcaagt                                                    78
```

<210> SEQ ID NO 35
<211> LENGTH: 78
<212> TYPE: DNA

<213> ORGANISM: Artificial Sequence
<220> FEATURE:
<223> OTHER INFORMATION: primer for pCG9ts-series vector preparation

<400> SEQUENCE: 35
ttgacaatta atcatcggct cgtataatgt gtggcttgcc aatccgatta gagcgtttta    60
gagctagaaa tagcaagt                                                  78

<210> SEQ ID NO 36
<211> LENGTH: 80
<212> TYPE: DNA
<213> ORGANISM: Artificial Sequence
<220> FEATURE:
<223> OTHER INFORMATION: ssODN sequence

<400> SEQUENCE: 36
ggtgccatgg gtgccaaaat gcgcaacatc ggcgaagctt cgacgaaggc gtcaccgtgg    60
gccccctggt tgaggaaaaa                                                80

<210> SEQ ID NO 37
<211> LENGTH: 80
<212> TYPE: DNA
<213> ORGANISM: Artificial Sequence
<220> FEATURE:
<223> OTHER INFORMATION: ssODN sequence

<400> SEQUENCE: 37
actggattga cggcgcgatt tccccatcca cttccggcaa gctgctaaga cgtggggcaa    60
cctgtctatc gctaagcgcc                                                80

<210> SEQ ID NO 38
<211> LENGTH: 80
<212> TYPE: DNA
<213> ORGANISM: Artificial Sequence
<220> FEATURE:
<223> OTHER INFORMATION: ssODN sequence

<400> SEQUENCE: 38
gactgttgtg gataactctt ctgcttggcg caaggacgac cagtgctgaa gccacttcac    60
gatgccgctg gtcttgtaaa                                                80

<210> SEQ ID NO 39
<211> LENGTH: 80
<212> TYPE: DNA
<213> ORGANISM: Artificial Sequence
<220> FEATURE:
<223> OTHER INFORMATION: ssODN sequence

<400> SEQUENCE: 39
gtcggtagct ttcaaaagct cgcttcgccg atgttgtggc cactcgccat caatcagtga    60
acacccatgc agtgcggttg                                                80

<210> SEQ ID NO 40
<211> LENGTH: 80
<212> TYPE: DNA
<213> ORGANISM: Artificial Sequence
<220> FEATURE:
<223> OTHER INFORMATION: ssODN sequence

<400> SEQUENCE: 40
ccacgattcc acccagtgga tgtccgcgct ctctgatgca cagagatcat ccacctggaa    60
gctggaaaat ccgttgcaga                                                80

<210> SEQ ID NO 41
<211> LENGTH: 80
<212> TYPE: DNA
<213> ORGANISM: Artificial Sequence
<220> FEATURE:
<223> OTHER INFORMATION: ssODN sequence

<400> SEQUENCE: 41
gtaaccacct tgcttcgggt atagaagttg aaagactcag gacttcgatg tccatctgaa    60
attctcgagc tgtacggcca                                                80

<210> SEQ ID NO 42
<211> LENGTH: 80
<212> TYPE: DNA
<213> ORGANISM: Artificial Sequence
<220> FEATURE:
<223> OTHER INFORMATION: ssODN sequence

<400> SEQUENCE: 42
gtcgagagta ctgacatgtc tgcatcagga aggataatcg cttgtctact ccggggtggc    60
ggacaagggc atcaccgaaa                                                80

<210> SEQ ID NO 43
<211> LENGTH: 80
<212> TYPE: DNA
<213> ORGANISM: Artificial Sequence
<220> FEATURE:
<223> OTHER INFORMATION: ssODN sequence

<400> SEQUENCE: 43
cttcgaagaa tccgaaagca ccgacctgcg tgccttcctg tcctggtttc ccgcgaggca    60
ctgtatgacg gtgctcgtct                                                80

<210> SEQ ID NO 44
<211> LENGTH: 80
<212> TYPE: DNA
<213> ORGANISM: Artificial Sequence
<220> FEATURE:
<223> OTHER INFORMATION: ssODN sequence

<400> SEQUENCE: 44
aacgatgttg actgctgctg cacgtgcacg acgcaggtcg ttggtgcgag gcagttggtg    60
gtgcaagatg cgccggagat                                                80

<210> SEQ ID NO 45
<211> LENGTH: 80
<212> TYPE: DNA
<213> ORGANISM: Artificial Sequence
<220> FEATURE:
<223> OTHER INFORMATION: ssODN sequence

<400> SEQUENCE: 45
ctgcaggatt tccacgagct tggtgttgga atgcacagct cgcccaaagg cacacggacc    60
tgcttcatct gaatgccgtt                                                80

<210> SEQ ID NO 46
<211> LENGTH: 80
<212> TYPE: DNA
<213> ORGANISM: Artificial Sequence
<220> FEATURE:
<223> OTHER INFORMATION: ssODN sequence

```
<400> SEQUENCE: 46
ggcatcaaca tcagcaatgg aagcttgttt gctttcggcg caaatgttgc agtcacaagg    60
tctcctaaag ttgattgtgg                                                80

<210> SEQ ID NO 47
<211> LENGTH: 80
<212> TYPE: DNA
<213> ORGANISM: Artificial Sequence
<220> FEATURE:
<223> OTHER INFORMATION: ssODN sequence

<400> SEQUENCE: 47
cccttgaaag tgcaaaagca tgctcgacgt cttgctcatc atgaagttct ttaggcagcg    60
gacctaaagg aagacgtttg                                                80

<210> SEQ ID NO 48
<211> LENGTH: 80
<212> TYPE: DNA
<213> ORGANISM: Artificial Sequence
<220> FEATURE:
<223> OTHER INFORMATION: ssODN sequence

<400> SEQUENCE: 48
ggaatgatct tgtcggatgc agcgcggttg atcagcttgc gccctctggg atgagatcgc    60
cgatgatgtt aatcagatac                                                80

<210> SEQ ID NO 49
<211> LENGTH: 48
<212> TYPE: DNA
<213> ORGANISM: Artificial Sequence
<220> FEATURE:
<223> OTHER INFORMATION: primer for pEK-pduyE preparation

<400> SEQUENCE: 49
acaatttcac acaggaaaca gaattcatga gatcgaaaag atttgaag                 48

<210> SEQ ID NO 50
<211> LENGTH: 46
<212> TYPE: DNA
<213> ORGANISM: Artificial Sequence
<220> FEATURE:
<223> OTHER INFORMATION: primer for pEK-pduyE preparation

<400> SEQUENCE: 50
aaaacagcca agcttggctg cagttaagca tggcgatccc gaaatg                   46

<210> SEQ ID NO 51
<211> LENGTH: 32
<212> TYPE: DNA
<213> ORGANISM: Artificial Sequence
<220> FEATURE:
<223> OTHER INFORMATION: primer for pEK-pduyE preparation

<400> SEQUENCE: 51
ttccaatgat gagcactttt ttgacaatta at                                  32

<210> SEQ ID NO 52
<211> LENGTH: 43
<212> TYPE: DNA
<213> ORGANISM: Artificial Sequence
<220> FEATURE:
<223> OTHER INFORMATION: primer for pEK-pduyE preparation

<400> SEQUENCE: 52
```

-continued

<210> SEQ ID NO 53
<211> LENGTH: 3895
<212> TYPE: DNA
<213> ORGANISM: Artificial Sequence
<220> FEATURE:
<223> OTHER INFORMATION: glpFKD

<400> SEQUENCE: 53

```
atgagtcaaa catcaacctt gaaaggccag tgcattgctg aattcctcgg taccgggttg      60
ttgattttct tcggtgtggg ttgcgttgca gcactaaaag tcgctggtgc gtcttttggt     120
cagtgggaaa tcagtgtcat ttggggactg ggggtggcaa tggccatcta cctgaccgca     180
ggggtttccg cgcgcatct taatcccgct gttaccattg cattgtggct gtttgcctgt     240
ttcgacaagc gcaaagttat tccttttatc gtttcacaag ttgccggcgc tttctgtgct     300
gcggctttag tttacgggct ttactacaat ttattttcg acttcgagca gactcatcac     360
attgttcgcg gcagcgttga agtgttgat ctggctggca ctttctctac ttaccctaat     420
cctcatatca attttgtgca ggctttcgca gttgagatgg tgattaccgc tattctgatg     480
gggctgatcc tggcgttaac ggacgatggc aacggtgtac cacgcggccc tttggctccc     540
ttgctgattg tctactgat tgcggtcatt ggcgcatcta tgggcccatt gacaggtttt     600
gccatgaacc cagcgcgtga cttcggtccg aaagtctttg cctggctggc gggctgggc     660
aatgtcgcct ttaccggcgg cagagacatt ccttacttcc tggtgccgct tttcggccct     720
atcgttggcg cgattgtagg tgcatttgcc taccgcaaac tgattggtcg ccatttgcct     780
tgcgatatct gtgttgtgga agaaaaggaa accacaactc cttcagaaca aaaagcttcg     840
ctgtaatatg actacgggac aattaaacat gactgaaaaa aaatatatcg ttgcgctcga     900
ccagggcacc accagctccc gcgcggtcgt aatggatcac gatgccaata tcattagcgt     960
gtcgcagcgc gaatttgagc aaatctaccc aaaaccaggt tgggtagaac acgacccaat    1020
ggaaatctgg gccacccaaa gctccacgct ggtagaagtg ctggcgaaag ccgatatcag    1080
ttccgatcaa attgcagcta tcggtattac gaaccagcgt gaaaccacta ttgtctggga    1140
aaaagaaacc ggcaagccta tctataacgc cattgtctgg cagtgccgtc gtaccgcaga    1200
aatctgcgag catttaaaac gtgacggttt agaagattat atccgcagca ataccggtct    1260
ggtgattgac ccgtactttt ctggcaccaa agtgaagtgg atcctcgacc atgtggaagg    1320
ctctcgcgag cgtgcacgtc gtggtgaatt gctgtttggt acggttgata cgtggcttat    1380
ctggaaaatg actcagggcc gtgtccatgt gaccgattac accaacgcct ctcgtaccat    1440
gttgttcaac atccataccc tggactggga cgacaaaatg ctggaagtgc tggatattcc    1500
gcgcgagatg ctgccagaag tgcgtcgttc ttccgaagta tacggtcaga ctaacattgg    1560
cggcaaaggc ggcacgcgta ttccaatctc cgggatcgcc ggtgaccagc aggccgcgct    1620
gtttggtcag ttgtgcgtga agaagggat ggcgaagaac acctatggca ctggctgctt    1680
tatgctgatg aacactggcg agaaagcggt gaaatcagaa acggcctgc tgaccaccat    1740
cgcctgcggc ccgactggcg aagtgaacta tgcgttggaa ggtgcggtgt ttatggcagg    1800
cgcatccatt cagtggctgc gcgatgaaat gaagttgatt aacgacgcct acgattccga    1860
atatttcgcc accaaagtgc aaaacaccaa tggtgtgtat gtggttccgg catttaccgg    1920
gctgggtgcg ccgtactggg acccgtatgc gcgcggggcg attttcggtc tgactcgtgg    1980
```

```
ggtgaacgct aaccacatta tacgcgcgac gctggagtct attgcttatc agacgcgtga      2040
cgtgctggaa gcgatgcagg ccgactctgg tatccgtctg cacgccctgc gcgtggatgg      2100
tggcgcagta gcaaacaatt tcctgatgca gttccagtcc gatattctcg gcacccgcgt      2160
tgagcgcccg gaagtgcgcg aagtcaccgc attgggtgcg gcctatctcg caggcctggc      2220
ggttggcttc tggcagaacc tcgacgagct gcaagagaaa gcggtgattg agcgcgagtt      2280
ccgtccaggc atcgaaacca ctgagcgtaa ttaccgttac gcaggctgga aaaaagcggt      2340
taaacgcgcg atggcgtggg aagaacacga cgaataaaag gagatataga tggaaaccaa      2400
agatctgatt gtgatagggg gcggcatcaa tggtgctggt atcgcggcag acgccgctgg      2460
acgcggttta tccgtgctga tgctggaggc gcaggatctc gcttgcgcga cctcttccgc      2520
cagttcaaaa ctcattcacg gtggcctgcg ctaccttgag cactatgaat ccgcctggt       2580 cagcgaggcg ctggctgaac gtgaagtgct gctgaaaatg gccccgcata tcgccttccc      2640
gatgcgtttt cgcctgccac atcgtccgca tctgcgcccg gcgtggatga ttcgcattgg      2700
tctgtttatg tacgatcatc tgggtaaacg caccagcttg ccgggatcaa ctggtttgcg      2760
ttttggcgca aattcagtgt taaaaccgga aattaagcgc ggattcgaat attctgactg      2820
ttgggtagac gacgcccgtc tggtactcgc caacgcccag atggtggtgc gtaaaggcgg      2880
cgaagtgctt actcggactc gcgccacctc tgctcgccgc gaaaacggcc tgtggattgt      2940
ggaagcggaa gatatcgata ccggcaaaaa atatagctgg caagcgcgcg gcttggttaa      3000
cgccaccggc ccgtgggtga acagttcttc gacgacggga tgcatctgc cttcgcctta       3060 tggcattcgc ctgatcaaag gcagccatat tgtggtgccg cgcgtgcata cccagaagca      3120
agcctacatt ctgcaaaacg aagataaacg tattgtgttc gtgatcccgt ggatggacga      3180
gttttccatc atcggcacta ccgatgtcga gtacaaaggc gatccgaaag cggtgaagat      3240
tgaagagagt gaaatcaatt acctgctgaa tgtgtataac acgcacttta aaaagcagtt      3300
aagccgtgac gatatcgtct ggacctactc cggtgtgcgt ccgctgtgtg atgatgagtc      3360
cgactcgccg caggctatta cccgtgatta caccccttgat attcatgatg aaaatggcaa      3420
agcaccgctg ctgtcggtat tcggcggtaa gctgaccacc taccgaaaac tggcggaaca      3480
tgcgctggaa aaactaacgc cgtattatca gggtattggc ccggcatgga cgaaagagag      3540
tgtgctaccg ggtggcgcca ttgaaggcga ccgcgacgat tatgccgctc gcctgcgccg      3600
ccgctatccg ttcctgactg aatcgctggc gcgtcattac gctcgcactt acggcagcaa      3660
cagcgagctg ctgctcggca atgcgggaac ggtaagcgat ctcggggaag atttcggtca      3720
tgagttctac gaagcggagc tgaaatacct ggtggatcac gaatgggtcc gccgcgccga      3780
cgacgccctg tggcgtcgca caaaacaagg catgtggcta aatgcggatc aacaatctcg      3840
tgtgagtcag tggctggtgg agtatacgca gcagaggtta tcgctggcgt cgtaa           3895
```

<210> SEQ ID NO 54
<211> LENGTH: 6538
<212> TYPE: DNA
<213> ORGANISM: Artificial Sequence
<220> FEATURE:
<223> OTHER INFORMATION: pCES208s-H36-S3

<400> SEQUENCE: 54

```
gatctttggg agcagtcctt gtgcgcttac gaggtgagcc ggtggggaac cgttatctgc        60
ctatggtgtg agcccccta gagagcttca agagcaatca gcccgaccta gaaaggaggc       120
caagagagag accccctacgg ggggaaccgt tttctgccta cgagatggca catttactgg      180
```

```
gaagctttac ggcgtcctcg tggaagttca atgcccgcag acttaagtgc tctattcacg    240
gtctgacgtg acacgctaaa ttcagacata gcttcattga ttgtcgccac gagccagtct    300
ctccctcaac agtcataaac caacctgcaa tggtcaagcg atttccttta gctttcctag    360
cttgtcgttg actggactta gctagttttt ctcgctgtgc tcgggcgtac tcactgtttg    420 ggtcttttcca gcgttctgcg gccttttttac cgccacgtct tcccatagtg ccagagctt    480 ttcgccctcg gctgctctgc gtctctgtct gacgagcagg gacgactggc tggccttttag   540 cgacgtagcc gcgcacacgt cgcgccatcg tctggcggtc acgcatcggc ggcagatcag    600
gctcacggcc gtctgctccg accgcctgag cgacggtgta ggcacgctcg taggcgtcga    660
tgatcttggt gtcttttagg cgctcaccag ccgcttttaa ctggtatccc acagtcaaag    720
cgtggcgaaa agccgtctca tcacgggcgg cacgccctgg agcagtccag aggacacgga    780
cgccgtcgat cagctctcca gacgcttcag cggcgctcgg caggcttgct tcaagcgtgg    840
caagtgcttt tgcttccgca gtggcttttc ttgccgcttc gatacgtgcc cgtccgctag    900
aaaactcctg ctcatagcgt tttttaggtt tttctgtgcc tgagatcatg cgagcaacct    960
ccataagatc agctaggcga tccacgcgat tgtgctgggc atgccagcgg tacgcggtgg   1020
gatcgtcgga gacgtgcagt ggccaccggc tcagcctatg tgaaaaagcc tggtcagcgc   1080
cgaaaacgcg ggtcatttcc tcggtcgttg cagccagcag gcgcatattc gggctgctca   1140
tgcctgctgc ggcatacacc ggatcaatga gccagatgag ctggcatttc ccgctcagtg   1200
gattcacgcc gatccaagct ggcgcttttt ccaggcgtgc ccagcgctcc aaaatcgcgt   1260
agacctcggg gtttacgtgc tcgattttcc cgccggcctg gtggctcggc acatcaatgt   1320
ccaggacaag cacggctgcg tgctgcgcgt cgtcagagc aacatactgg caccgggcaa   1380 gcgatttga accaactcgg tataacttcg gctgtgtttc cccgtgtcc gggtctttga    1440 tccaagcgct ggcgaagtcg cgggtcttgc tgccctggaa attttctctg cccaggtgag   1500
cgaggaattc gcggcggtct tcgctcgtcc agccacgtga tcgcagcgcg agctcggat    1560 gggtgtcgaa cagatcagcg gaaaatttcc aggccggtgt gtcaatgtct cgtgaatccg   1620
ctagagtcat ttttgagcgc tttctcccag gtttggactg ggggttagcc gacgccctgt   1680
gagttaccgc tcacggggcg ttcaacattt ttcaggtatt cgtgcagctt atcgcttctt   1740
gccgcctgtg cgcttttttcg acgcgcgacg ctgctgccga ttcggtgcag gtggtggcgg   1800
cgctgacacg tcctgggcgg ccacggccac acgaaacgcg gcatttacga tgtttgtcat   1860
gcctgcgggc accgcgccac gatcgcggat aattctcgct gccgcttcca gctctgtgac   1920
gaccatggcc aaaatttcgc tcggggacg cacttccagc gccatttgcg acctagccgc    1980
ctccagctcc tcggcgtggc gtttgttggc gcgctcgcgg ctggctgcgg cacgacacgc   2040
atctgagcaa tattttgcgc gccgtcctcg cgggtcaggc cggggaggaa tcaggccacc   2100
gcagtaggcg caactgattc gatcctccac tactgtgcgt cctcctggcg ctgccgagca   2160
cgcagctcgt cagccagctc ctcaagatcc gccacgagag tttctaggtc gctcgcggca   2220
ctggcccagt ctcgtgatgc tggcgcgtcc gtcgtatcga gagctcggaa aaatccgatc   2280
accgttttta aatcgacggc agcatcgagc gcgtcggact ccagcgcgac atcagagaga   2340
tccatagctg atgattcggg ccaatttttgg tacttcgtcg tgaaggtcat gacaccatta   2400
taacgaacgt tcgttaaagt ttttggcgga aaatacgcg gcacgaaaat ttcacgaag     2460 cgggactttg cgcagctcag gggtgctaaa aattttgtat cgcacttgat ttttccgaaa   2520
```

```
gacagattat ctgcaaacgg tgtgtcgtat ttctggcttg gttttaaaa aatctggaat    2580
cgaaaatttg cggggcgacc gagaagtttt ttacaaaagg caaaaacttt ttcgggatcg    2640
acagaaataa aacgatcgac ggtacgcaac aaaaaagcgt caggatcgcc gtagagcgat    2700
tgaagaccgt caaccaaagg ggaagcctcc aatcgacgcg acgcgcgctc tacggcgatc    2760
ctgacgcaga tttttagcta tctgtcgcag cgccctcagg gacaagccac ccgcacaacg    2820
tcgcgagggc gatcagcgac gccgcagtac tgatcctccg gcgttcagcc tgtgccacag    2880
ccgacaggat ggtgaccgcg caattaaccc tcactaaagg gaacaaaagc tgggtaccgg    2940
gccccccctc gaggtcgacg gtacctctat ctggtgccct aaacggggga atattaacgg    3000
gcccagggtg gtcgcacctt ggttggtagg agtagcatgg gatcctctag aggcccagcc    3060
ggccattata attaggcctc gggggccgcg ccgctgcct ggcggcagta gcgcggtggt    3120
cccacctgac cccatgccga actcagaagt gaaacgccgt agcgccgatg gtagtgtggg    3180
gtctccccat gcgagagtag ggaactgcca ggcatcaaat aaaacgaaag gctcagtcga    3240
aagactgggc ctttcgtttt atctgttgtt tgtcggtgaa cgctctcctg agtaggacaa    3300
atccgccggg agcggatttg aacgttgcga gcaacggcc cggagggtgg cgggcaggac    3360
gcccgccata aactgccagg catcaaatta agcagaaggc catcctgacg gatggccttt    3420
tgccaccgcg gtggagctcc aattcgccct atagtgagtc gtattacgcg cggtgaccac    3480
catttgcccc atatcaccgt cggtactgat cccgtcgtca ataaaccgaa ccgctacacc    3540
ctgagcatca aactcttta tcagttggat catgtcggcg gtgtcgcggc caagacggtc    3600
gagcttcttc accagaatga catcaccttc ctccaccttc atcctcagca aatccagccc    3660
ttcccgatct gttgaactgc cggatgcctt gtcggtaaag atgcggttag cttttacccc    3720
tgcatctttg agcgctgagg tctgcctcgt gaagaaggtg ttgctgactc ataccaggcc    3780
tgaatcgccc catcatccag ccagaaagtg agggagccac ggttgatgag agctttgttg    3840
taggtggacc agttggtgat tttgaacttt tgctttgcca cggaacggtc tgcgttgtcg    3900
ggaagatgcg tgatctgatc cttcaactca gcaaaagttc gatttattca acaaagccgc    3960
cgtcccgtca gtcagcgta atgctctgcc agtgttacaa ccattcaaat atgtatccgc    4020
tgagcaataa ctagcataac cccttggggc ctctaaacgg gtcttgaggg gttttttgct    4080
gaaacctcag gcatttgaga agcacacggt cacactgctt ccggtagtca ataaaccggt    4140
aaaccagcaa tagacataag cggctattta acgaccctgc cctgaaccga cgaccgggtc    4200
atcgtggccg gatcttgcgg cccctcgct tgaacgaatt gttagacatt atttgccgac    4260
taccttggtg atctcgcctt tcacgtagtg gacaaattct tccaactgat ctgcgcgcga    4320
ggccaagcga tcttcttctt gtccaagata agcctgtcta gcttcaagta tgacgggctg    4380
atactgggcc ggcaggcgct ccattgccca gtcggcagcg acatccttcg gcgcgatttt    4440
gccggttact gcgctgtacc aaatgcggga caacgtaagc actacatttc gctcatcgcc    4500
agcccagtcg ggcggcgagt tccatagcgt taaggtttca tttagcgcct caaatagatc    4560
ctgttcagga accggatcaa agagttcctc cgccgctgga cctaccaagg caacgctatg    4620
ttctcttgct tttgtcagca agatagccag atcaatgtcg atcgtggctg gctcgaagat    4680
acctgcaaga atgtcattgc gctgccattc tccaaattgc agttcgcgct tagctggata    4740
acgccacgga atgatgtcgt cgtgcacaac aatggtgact tctacagcgc ggagaatctc    4800
gctctctcca ggggaagccg aagttttcca aaggtcgttg atcaaagctc gccgcgttgt    4860
ttcatcaagc cttacggtca ccgtaaccag caaatcaata tcactgtgtg gcttcaggcc    4920
```

```
gccatccact gcggagccgt acaaatgtac ggccagcaac gtcggttcga gatggcgctc    4980
gatgacgcca actacctctg atagttgagt cgatacttcg gcgatcaccg cttccctcat    5040
actcttcctt tttcaatatt attgaagcat ttatcagggt tattgtctca tgagcggata    5100
catatttgaa tgtatttaga aaaataaaca aatagctagc tcactcggtc ggagtgtata    5160
ctggcttact atggctgagt tgaaggatca gatcacgcat cttcccgaca acgcagaccg    5220
ttccgtggca aagcaaaagt tcaaaatcac caactggtcc acctacaaca aagctctcat    5280
caaccgtggc tccctcactt tctggctgga tgatggggcg attcaggcct ggtatgagtc    5340
agcaacacct tcttcacgag gcagacctca gcgctagcgg agtgtatact ggcttactat    5400
gttggcactg atgagggtgt cagtgaagtg cttcatgtgg caggagaaaa aaggctgcac    5460
cggtgcgtca gcagaatatg tgatacagga tatattccgc ttcctcgctc actgactcgc    5520
tacgctcggt cgttcgactg cggcgagcgg aaatggctta cgaacggggc ggagatttcc    5580
tggaagatgc caggaagata cttaacaggg aagtgagagg gccgcggcaa agccgttttt    5640
ccataggctc cgcccccctg acaagcatca cgaaatctga cgctcaaatc agtggtggcg    5700
aaacccgaca ggactataaa gataccaggc gtttccccct ggcggctccc tcgtgcgctc    5760
tcctgttcct gcctttcggt ttaccggtgt cattccgctg ttatggccgc gtttgtctca    5820
ttccacgcct gacactcagt tccgggtagg cagttcgctc caagctggac tgtatgcacg    5880
aaccccccgt tcagtccgac cgctgcgcct tatccggtaa ctatcgtctt gagtccaacc    5940
cggaaagaca tgcaaaagca ccactggcag cagccactgg taattgattt agaggagtta    6000
gtcttgaagt catgcgccgg ttaaggctaa actgaaagga caagttttgg tgactgcgct    6060
cctccaagcc agttacctcg gttcaaagag ttggtagctc agagaacctt cgaaaaaccg    6120
ccctgcaagg cggttttttc gttttcagag caagagatta cgcgcagacc aaaacgatct    6180
caagaagatc atcttattaa ggggtctgac gctcagtgga acgaaaactc acgttaaggg    6240
attttggtca tgagattatc aaaaaggatc ttcacctaga tccttttaaa ttaaaaatga    6300
agttttaaat caatctaaag tatatatgag taaacttggt ctgacagtta ccaatgctta    6360
atcagtgagg cacctatctc agcgatctgt ctatttcgtt catccatagt tgcctgactc    6420
cccgtcgtgt agataactac gatacgggag ggcttaccat ctggccccag tgctgcaatg    6480
ataccgcgag acccacgctc accggctcca gatttatcag caataaacca gccagccg    6538
```

<210> SEQ ID NO 55
<211> LENGTH: 2856
<212> TYPE: DNA
<213> ORGANISM: Artificial Sequence
<220> FEATURE:
<223> OTHER INFORMATION: pUC19-sgRNA

<400> SEQUENCE: 55

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgttttagag ctagaaatag     420
```

-continued

| | | | | | |
|---|---|---|---|---|---|
| caagttaaaa | taaggctagt | ccgttatcaa | cttgaaaaag | tggcaccgag | tcggtgcttc | 480 |
| actcgagcca | ggcatcaaat | aaaacgaaag | gctcagtcga | aagactgggc | ctttcgtttt | 540 |
| atctgttgtt | tgtcggtgaa | cgctctctac | tagagtcaca | ctggctcacc | ttcgggtggg | 600 |
| cctttctgcg | tttataaagc | ttggcgtaat | catggtcata | gctgtttcct | gtgtgaaatt | 660 |
| gttatccgct | cacaattcca | cacaacatac | gagccggaag | cataaagtgt | aaagcctggg | 720 |
| gtgcctaatg | agtgagctaa | ctcacattaa | ttgcgttgcg | ctcactgccc | gctttccagt | 780 |
| cgggaaacct | gtcgtgccag | ctgcattaat | gaatcggcca | acgcgcgggg | agaggcggtt | 840 |
| tgcgtattgg | gcgctcttcc | gcttcctcgc | tcactgactc | gctgcgctcg | tcgttcggc | 900 |
| tgcggcgagc | ggtatcagct | cactcaaagg | cggtaatacg | gttatccaca | gaatcagggg | 960 |
| ataacgcagg | aaagaacatg | tgagcaaaag | gccagcaaaa | ggccaggaac | cgtaaaaagg | 1020 |
| ccgcgttgct | ggcgtttttc | cataggctcc | gcccccctga | cgagcatcac | aaaaatcgac | 1080 |
| gctcaagtca | gaggtggcga | aacccgacag | gactataaag | ataccaggcg | tttccccctg | 1140 |
| gaagctccct | cgtgcgctct | cctgttccga | ccctgccgct | taccggatac | ctgtccgcct | 1200 |
| ttctcccttc | gggaagcgtg | gcgctttctc | atagctcacg | ctgtaggtat | ctcagttcgg | 1260 |
| tgtaggtcgt | tcgctccaag | ctgggctgtg | tgcacgaacc | ccccgttcag | cccgaccgct | 1320 |
| gcgccttatc | cggtaactat | cgtcttgagt | ccaacccggt | aagacacgac | ttatcgccac | 1380 |
| tggcagcagc | cactggtaac | aggattagca | gagcgaggta | tgtaggcggt | gctacagagt | 1440 |
| tcttgaagtg | gtggcctaac | tacggctaca | ctagaaggac | agtatttggt | atctgcgctc | 1500 |
| tgctgaagcc | agttaccttc | ggaaaaagag | ttggtagctc | ttgatccggc | aaacaaacca | 1560 |
| ccgctggtag | cggtggtttt | tttgtttgca | agcagcagat | tacgcgcaga | aaaaaggat | 1620 |
| ctcaagaaga | tcctttgatc | ttttctacgg | ggtctgacgc | tcagtggaac | gaaaactcac | 1680 |
| gttaagggat | tttggtcatg | agattatcaa | aaaggatctt | cacctagatc | cttttaaatt | 1740 |
| aaaaatgaag | ttttaaatca | atctaaagta | tatatgagta | aacttggtct | gacagttacc | 1800 |
| aatgcttaat | cagtgaggca | cctatctcag | cgatctgtct | atttcgttca | tccatagttg | 1860 |
| cctgactccc | cgtcgtgtag | ataactacga | tacgggaggg | cttaccatct | ggccccagtg | 1920 |
| ctgcaatgat | accgcgagac | ccacgctcac | cggctccaga | tttatcagca | ataaaccagc | 1980 |
| cagccggaag | ggccgagcgc | agaagtggtc | ctgcaacttt | atccgcctcc | atccagtcta | 2040 |
| ttaattgttg | ccgggaagct | agagtaagta | gttcgccagt | taatagtttg | cgcaacgttg | 2100 |
| ttgccattgc | tacaggcatc | gtggtgtcac | gctcgtcgtt | tggtatggct | tcattcagct | 2160 |
| ccggttccca | acgatcaagg | cgagttacat | gatcccccat | gttgtgcaaa | aaagcggtta | 2220 |
| gctccttcgg | tcctccgatc | gttgtcagaa | gtaagttggc | cgcagtgtta | tcactcatgg | 2280 |
| ttatggcagc | actgcataat | tctcttactg | tcatgccatc | cgtaagatgc | ttttctgtga | 2340 |
| ctggtgagta | ctcaaccaag | tcattctgag | aatagtgtat | gcggcgaccg | agttgctctt | 2400 |
| gcccggcgtc | aatacgggat | aataccgcgc | cacatagcag | aactttaaaa | gtgctcatca | 2460 |
| ttggaaaacg | ttcttcgggg | cgaaaactct | caaggatctt | accgctgttg | agatccagtt | 2520 |
| cgatgtaacc | cactcgtgca | cccaactgat | cttcagcatc | ttttactttc | accagcgttt | 2580 |
| ctgggtgagc | aaaaacagga | aggcaaaatg | ccgcaaaaaa | gggaataagg | gcgacacgga | 2640 |
| aatgttgaat | actcatactc | ttcctttttc | aatattattg | aagcatttat | cagggttatt | 2700 |
| gtctcatgag | cggatacata | tttgaatgta | tttagaaaaa | taaacaaata | ggggttccgc | 2760 |
| gcacatttcc | ccgaaaagtg | ccacctgacg | tctaagaaac | cattattatc | atgacattaa | 2820 |

```
cctataaaaa taggcgtatc acgaggccct ttcgtc                              2856
```

<210> SEQ ID NO 56
<211> LENGTH: 1473
<212> TYPE: DNA
<213> ORGANISM: Artificial Sequence
<220> FEATURE:
<223> OTHER INFORMATION: NCgl0049

<400> SEQUENCE: 56

```
atgactatta atgtctccga actacttgcc aaagtcccca cgggtctact gattggtgat    60
tcctgggtgg aagcatccga cggcggtact ttcgatgtgg aaaacccagc gacgggtgaa   120
acaatcgcaa cgctcgcgtc tgctacttcc gaggatgcac tggctgctct tgatgctgca   180
tgcgctgttc aggccgagtg ggctaggatg ccagcgcgcg agcgttctaa tattttacgc   240
cgcggttttg agctcgtagc agaacgtgca gaaagagttcg ccaccctcat gaccttggaa   300
atgggcaagc cttggctga agctcgcggc gaagtcacct acggcaacga attcctgcgc   360
tggttctctg aggaagcagt tcgtctgtat ggccgttacg gaaccacacc agaaggcaac   420
ttgcggatgc tgaccgccct caagccagtt ggcccgtgcc tcctgatcac cccatggaac   480
ttcccactag caatggctac ccgcaaggtc gcacctgcga tcgctgcagg ttgtgtcatg   540
gtgctcaagc cagctcgact taccccgctg acctcccagt attttgctca gaccatgctt   600
gatgccggtc ttccagcagg tgtcctcaat gtggtctccg gtgcttccgc ctctgcgatt   660
tccaacccga ttatggaaga cgatcgcctt cgtaaagtct ccttcaccgg ctccaccca   720
gttggccagc agctgctcaa aaaggctgcc gataaagttc tgcgcacctc catggaactt   780
ggtggcaacg caccttttcat tgtcttcgag gacgccgacc tagatctcgc gatcgaaggt   840
gccatgggtg ccaaaatgcg caacatcggc gaagcttgca ccgcagccaa ccgtttctta   900
gtccacgaat ccgtcgccga tgaattcggc cgtcgcttcg ctgcccgcct tgaagagcaa   960
gtcctaggca acggcctcga cgaaggcgtc accgtgggcc cctggttga ggaaaaagca  1020
cgagacagcg ttgcatcgct tgtcgacgcc gccgtcgccg aaggtgccac cgtcctcacc  1080
ggcggcaagg ccggcacagg tgcaggctac ttctacgaac caacggtgct cacgggagtt  1140
tcaacagatg cggctatcct gaacgaagag atcttcggtc ccgtcgcacc gatcgtcacc  1200
ttccaaaccg aggaagaagc cctgcgtcta gccaactcca ccgaatacgg actgcctcc  1260
tatgtgttca cccaggacac ctcacgtatt ttccgcgtct ccgatggtct cgagttcggc  1320
ctagtgggcg tcaattccgg tgtcatctct aacgctgctg cacctttggg tggcgtaaaa  1380
caatccggaa tgggccgcga aggtggtctc gaaggaatcg aggagtacac ctccgtgcag  1440
tacatcggta tccgggatcc ttacgccggc tag                                1473
```

<210> SEQ ID NO 57
<211> LENGTH: 1515
<212> TYPE: DNA
<213> ORGANISM: Artificial Sequence
<220> FEATURE:
<223> OTHER INFORMATION: NCgl0157

<400> SEQUENCE: 57

```
atgtctgaac cacaaaccat ctcgcactgg attgacggcg cgatttcccc atccacttcc    60
ggcaagaccg ctcctgtcta caatcctgca actggccagg tcaccgccaa tgttgcgctg   120
gctagccagg aagagatcga tgccaccatc gcttctgcca ccaaggctgc taagacgtgg   180
```

```
ggcaacctgt ctatcgctaa gcgccaagct gtgcttttca acttccgtga gctgctgaat    240
gctcgcaagg gtgagctggc ggagatcatc actgcagagc acggcaaggt cttgtccgat    300
gccatgggtg aaatcctgcg cggccaggaa gtcgtggagc ttgctaccgg tttcccacac    360
ctgcttaaag gtgcgttcaa cgagaacgtc tccaccggca ttgatgtgta ttccttgaag    420
cagccactgg gtgttgtcgg tatcatcagc ccgttcaact ccctgcgat ggtgccgatg     480 tggttttttcc caatcgcaat cgctgcaggc aacgcagtta ttttgaagcc ttcagagaag    540
gatccttcgg cagcgctgtg gatggctcag atctggaagg aagctggtct tccagacggc    600
gtattcaacg tgctccaggg cgacaagctg gctgttgatg gtttgctgaa cagccctgat    660
gtctctgcga tttccttcgt gggttccacc ccaatcgcaa agtacatcta cgagacttcc    720
gcgaagaacg gcaagcgcgt ccaggcgttg ggcggcgcga agaaccacat gctggtgctg    780
ccagatgctg atctggatct ggttgccgat caggcaatca acgcaggtta cggcgctgcc    840
ggtgagcgtt gcatggctgt ttctgtggtc ttggctattg aatctgttgc cgacgagctc    900
attgagaaga tcaaggagcg catcgacacc ctgcgcatcg caacggtgc cggcgacgag     960 cagggcgagc cgcacctggg cccactaatc accgacgtcc accgcgacaa ggtcgcttct   1020
tatgtcgaca tcgctgaggc cgacggcgcc aagatcatcg tggacgggcg taactgcgcc   1080
gtagacgggc acgaggaggg cttcttcttc ggccctacgc ttatcgacga catcccactc   1140
acgtcccgcg cctacaccga gaaaatcttc ggcccggtcc tctctgtcgt tcgtgtcgca   1200
tccttcgacg aggcaattga gctgatcaac tccggtgaat tcggcaacgg aaccgcaatc   1260
ttcaccaaca atggtggagc ggcacgccgc ttccagcatg agatcgaagt gggcatgatc   1320
ggcatcaacg taccaatccc agtgcctgtt gcgtaccact ccttcggtgg ttggaagaac   1380
tccctcttcg gtgacgccaa ggcatatggc actcaaggtt ttgattctt caccagggaa    1440 aaggcgatca ccagccgttg gctcgaccca gcaacccacg gtggcattaa cctcggtttc   1500
ccacagaacg attaa                                                    1515

<210> SEQ ID NO 58
<211> LENGTH: 1035
<212> TYPE: DNA
<213> ORGANISM: Artificial Sequence
<220> FEATURE:
<223> OTHER INFORMATION: NCgl0248

<400> SEQUENCE: 58
atgaccacca tcgcagttgt tggtgcaacc ggccaggtcg ccaggttat gcgcaccctt      60 ttggaagagc gcaatttccc agctgacact gttcgtttct ttgcttcccc acgttccgca    120
ggccgtaaga ttgaattccg tggcacggaa atcgaggtag aagacattac tcaggcaacc    180
gaggagtccc tcaaggacat cgacgttgcg ttgttctccg ctggaggcac cgcttccaag    240
cagtacgctc cactgttcgc tgctgcaggc gcgactgttg tggataactc ttctgcttgg    300
cgcaaggacg acgaggttcc actaatcgtc tctgaggtga acccttccga caaggattcc    360
ctggtcaagg gcattattgc gaaccctaac tgcaccacca tggctgcgat gccagtgctg    420
aagccacttc acgatgccgc tggtcttgta aagcttcacg tttcctctta ccaggctgtt    480
tccggttctg gtcttgcagg tgtggaaacc ttggcaaagc aggttgctgc agttggagac    540
cacaacgttg agttcgtcca tgatggacag gctgctgacg caggcgatgt cggaccttat    600
gtttcaccaa tcgcttacaa cgtgctgcca ttcgccggaa acctcgtcga tgacggcacc    660
ttcgaaaccg atgaagagca gaagctgcgc aacgaatccc gcaagattct cggtctccca    720
```

```
gacctcaagg tctcaggcac ctgcgtccgc gtgccggttt tcaccggcca cacgctgacc    780
attcacgccg aattcgacaa ggcaatcacc gtggaccagg cgcaggagat cttgggtgcc    840
gcttcaggcg tcaagcttgt cgacgtccca accccacttg cagctgccgg cattgacgaa    900
tccctcgttg gacgcatccg tcaggactcc actgtcgacg ataaccgcgg tctggttctc    960
gtcgtatctg gcgacaacct ccgcaagggt gctgcgctaa acaccatcca gatcgctgag   1020
ctgctggtta agtaa                                                    1035
```

<210> SEQ ID NO 59
<211> LENGTH: 1563
<212> TYPE: DNA
<213> ORGANISM: Artificial Sequence
<220> FEATURE:
<223> OTHER INFORMATION: NCgl0437

<400> SEQUENCE: 59

```
atgatcaccg caaccgcact gcatgggtgt tcactgattg atggcgagtg ggtcgctgga     60
aaaaatggtg agattacagg attcgatccg cgcaccaatg cgagtctgaa cccttcctac    120
tctttagcaa acagcgcaca gctgcgcgcc gccacaacat cggcgaagcg agcttttgaa    180
agctaccgac tcactactcc agaggttaga gcagatttcc tggattccat cgctgacaac    240
atcgatgcgc tatccggcga gatcgtgcaa cgggcgagcc tggagacagg tttgggaact    300
acccgactca caggcgaagt agcccgcacc agcaaccagc tccgcctgtt tgcagaaacc    360
gtgagaagcg gacagttcca ccgagtacgc attgaacgag accgcggat tgatcttcgc    420 cagcgtcagg ttccgttggg accagtcgcg gtattcgggg caagcaactt ccccgtcgct    480
ttctctactg ctggtggcga tacagcatca gcgttggctg caggctgccc tgtggttttt    540
aaggcgcata atgcgcaccc tggaacagct gagctcgtcg ggcaagcggt gcggggagcc    600
gtcgaaaagc atgagtttga tgctggtgtg tttaaccttg tctacggccg tggcgtggaa    660
attggccagg agctggctgc ggatccgaat atcacggcaa tcggttttac cggttcacgc    720
cagggtggtt tggcactgtc acagactgcg tttagccgcc cagttcccgt tccagtcttt    780
gcagaaatga gtgccaccaa ccctgtgttc gtcttccccg cgcgctggc ggatttggat    840 gcatcgagtt ccttggctga ggcgtttacc gcttccgtca ccggcagttc cgggcaattg    900
tgcaccaagc ctggcctcgt tttcatcccg cgcggtgttg ttggtgatgc ttttgtggcg    960
ctcgtagcag ccaaatttaa agaaaccacg ggtcaaacga tgctcacgca aggcatcgct   1020
caggcatggc agcgcggagt cgacaacctt gcagcacagc caagtgtaaa aatcctcgcc   1080
caaggcaccc ccggagatgg agaaacgcg ccgggcccgg tggtgtttga agtgatgtg    1140 caggcgttgc taaataatgt ggtgttgcag gaagaaatct tcggtgcggc atcgctggtg   1200
gtgcgttatg attccccgga tcaactccac caagtagcca attcactcga gggacaatta   1260
acagccacga tccacgcatc ccaggatgat ttccaggaag tctcgaaact tatccccctc   1320
ttggaggatc tcgcgggccg tgttctttac ggcggctggc aacgggtgt ggaagttggg    1380 cacacggtta tccatggagg cccttatccg gcgacctcaa atgcgcagtc gacaagtgtt   1440
ggaaccctgg caatcgagag atttatgcgc ccggtttctt atcaaacttt cccggctgag   1500
ctgcttccag atccagtttc tgaggcgaat aaatgggctg tacctcggga aatagaccgt   1560
taa                                                                1563
```

<210> SEQ ID NO 60

<211> LENGTH: 1362
<212> TYPE: DNA
<213> ORGANISM: Artificial Sequence
<220> FEATURE:
<223> OTHER INFORMATION: NCgl0463

<400> SEQUENCE: 60

| | | | | | |
|---|---|---|---|---|---|
| gtgtctttga | ccttcccagt | aatcaacccc | agcgatggct | ccaccatcac | cgagctagaa | 60 |
| aaccacgatt | ccacccagtg | gatgtccgcg | ctctctgatg | cagttgcagc | tggtccttca | 120 |
| tgggctgcga | aaactccccg | cgaaagatcc | gtggtactca | ccgcaatctt | cgaagcactg | 180 |
| accgaacgcg | cccaagaact | tgcagagatc | atccacctgg | aagctggaaa | atccgttgca | 240 |
| gaagctcttg | gtgaagtcgc | ttatggtgca | gaatacttcc | gttggtttgc | ggaagaagca | 300 |
| gtgcgcctgc | ccggccgcta | cggacagtca | ccttccggaa | tcggtcacat | cgccgtcacc | 360 |
| cgcgcacccg | tgggaccagt | gctggcgatc | accccatgga | atttccccat | cgccatggcc | 420 |
| acccgcaaaa | tcgccccagc | cctggccgct | ggttgcsccg | tgttggtgaa | acctgcttcc | 480 |
| gaaaccccac | tgaccatggt | caaagtgggg | gagatcatcc | cctccgtctt | tgatacccttt | 540 |
| aatatcccgc | agggcttggt | ctcaatcatc | accaccactc | gagatgcaga | gctatcggca | 600 |
| gaactcatgg | ctgatcctcg | cttggctaaa | gtcaccttca | ctggatcaac | caacgtggga | 660 |
| cgcatcctgg | tccgccaatc | cgcggaccga | ctgctgcgca | cctccatgga | actcggcgga | 720 |
| aatgcagctt | ttgttatcga | cgaagccgca | gacctcgacg | aagccgtatc | cggtgccatc | 780 |
| gccgcaaaac | tccgcaacgc | cggccaagta | tgcatcgcag | ctaaccgttt | cttggttcat | 840 |
| gaatcccgcg | ctgccgaatt | cacctcaaag | ctggcgacag | ccatgcagaa | cactcccatt | 900 |
| gggccggtga | tttctgcccg | ccaacgcgac | cggatcgcag | cactagtgga | tgaagccatc | 960 |
| accgacggcg | cccgcctcat | catcggtggg | gaggtccccg | acggctccgg | cttcttctat | 1020 |
| ccagccacca | tcttggccga | tgtccctgca | cagtcacgga | ttgtgcatga | ggaaatcttc | 1080 |
| ggacctgtgg | ccaccattgc | cactttcacc | gacttggccg | aaggcgttgc | acaagcaaat | 1140 |
| tccaccgaat | tcggcctcgc | agcctacgga | ttcagcaaca | atgtgaaagc | aacacagtac | 1200 |
| atggcggaac | acttggaagc | cggaatggtc | ggaatcaaca | gaggcgccat | ctctgaccca | 1260 |
| gcagcacctt | ttggcggcat | cggacaatcc | ggcttcggca | gagaaggcgg | aaccgaagga | 1320 |
| atcgaagaat | atctctccgt | gcgttacctc | gctttgccgt | ga | | 1362 |

<210> SEQ ID NO 61
<211> LENGTH: 324
<212> TYPE: DNA
<213> ORGANISM: Artificial Sequence
<220> FEATURE:
<223> OTHER INFORMATION: NCgl0521

<400> SEQUENCE: 61

| | | | | | |
|---|---|---|---|---|---|
| ttggaaagtt | ccaattctca | ggcacaggga | cgtgcggaca | gaattctcga | ttcagccttg | 60 |
| aaagaaggcg | cttcaatagt | tgttgatggc | cgtacagctc | gagaatttca | gatggacatc | 120 |
| gaagtcggaa | tggttggcat | taacgtgcca | atcccagtcc | caattggcgc | tttctcattt | 180 |
| ggaggttgga | aagactcact | attcggagac | acacacatgt | atggatctga | gtctttcaac | 240 |
| ttctataccc | gaagcaaggt | ggttaccact | cgctggcctc | ttccaaatga | atcacagatt | 300 |
| gagcttggct | tccccaccca | ctaa | | | | 324 |

<210> SEQ ID NO 62
<211> LENGTH: 1494

```
<212> TYPE: DNA
<213> ORGANISM: Artificial Sequence
<220> FEATURE:
<223> OTHER INFORMATION: NCgl0523

<400> SEQUENCE: 62
atgaatgctg caaccaggcg tgcttctctg caactcccct atacccatgt cgatgatttc      60
tacatcaacg gttcctgggt taaagcagaa ggaacacaac gcaacccgt agttgatcct      120
gcggtcggtc aagaatgggg atctgttcca gaagcaaccg catctgaatt ggactctgcg      180
gtgggagctg cacgtacagc gctaaagtcg tggagtgcac ttacaggtgc ggaacgaaca      240
ggctacctcc tgaaaatcgc gacggaaatt gaatcccgtt ctgaagctct agcacttact      300
aatacccgcg aaaatggttc ccccatttcc gagacccgtg agctgcgtc caatgcagca      360
ggaattttcc gttactttgc cactctcgcg ccttggttag acggcgaaga catccgccca      420
tttcctgccg gtagcgccga atccatcgtg ataaagatc ccatcggtgt ctgcgcactc      480
atcgccccat ggaatttccc gatcaacctt gtagtcatca aactggcacc agcacttctt      540
gccggctgta ccgtcatcat caaaccagcc tcccccaccc cactgtcgat ccgtttcatc      600
atcgaagcca tcgaagccgc cggagtgcca gcaggcgtag tcaacctact caccggttca      660
gggcgtttcg gtgatgccct tgtccgccac cccggagtag acaaggtagc gtttaccgga      720
tcaacgcctg ttggaaagaa gatcgctgcc gcctgcggag aactactccg accagtgact      780
ttagagctag gcggaaaatc ttccgcgatt atccttcctg atgcagacat gtcagtactc      840
tcgacgcggt tgattcgatc ctgtatgcgc aacactggac aaaacctgcta catcagtacc      900
cggattattg cccctagctc acgctatgcg gaagtcgtac aaacagtggc aagcactatc      960
gctgcaggta gacaaggtga cccctatgat gaagaaacgg tttttgggcc agttgccagc      1020
gcctctcagt actcaaccgt catgtcttac attgactccg cacgagagga aggtgcacga      1080
gtggttgcag gtggaacccg gtcaatcagc cttttctgaag gtttagaatc aggcgagttt      1140
atccaaccaa ccgtgtttgc cgatgtcacc cccgacatgc ggatatcacg cgaagaaatc      1200
ttcggccctg ttatttccat cctaaagtac gacgatacaa acggtgtttc cgaagcaatc      1260
gcactagcca acaacacgaa attcggtctc ggtggcttgg tatttggtgc ggatgaggaa      1320
caagcactag aagtcgcccg tcaagtggat tctggttccg taggcatcaa cttcttcggt      1380
tccaaccatt ccgccccatt tggaggacgc acgaatccg gtatgggagt ggaatacggc      1440
atcgaaggcc tcagtgctta cctgacatac aagagtattc accgaaccat ttag            1494

<210> SEQ ID NO 63
<211> LENGTH: 1443
<212> TYPE: DNA
<213> ORGANISM: Artificial Sequence
<220> FEATURE:
<223> OTHER INFORMATION: NCgl0900

<400> SEQUENCE: 63
atgacgcaca accacaagga ctggaacgat cgcattgcag ttgcggagga aatggtgccg      60
ttgatcgggc gcctgcaccg caacaacaac gtggtggttt ccgtattcgg tcgtctcctt      120
gtgaatgtct cagacatcga tatcatcaag tctcaccgct acgcccgcca catcatatcc      180
aaggaacttc cactggaaag ctccttggat attttgcgcg aactggtaga tatgaacctt      240
ggtaccgcat cgatcgacct gggacagctg gcctacagct tcgaagaatc cgaaagcacc      300
gacctgcgtg ccttcctgga ggacgctctc gcgccggtca ttggtgcgga aaccgacatc      360
```

```
aacccaactg atatcgtgct gtacggtttc ggccgcatcg gtcgcctgct ggcccgcatc    420
ctggtttccc gcgaggcact gtatgacggt gctcgtctgc gcgccatcgt ggtccgcaaa    480
aatggtgaag aagacctggt caagcgcgca tccttgctgc gtcgtgattc tgtccacggt    540
ggattcgatg gcaccatcac caccgattat gacaacaaca tcatctgggc caacggcacc    600
ccaatcaagg tcatctactc caatgaccca gccaccattg attacaccga atacggcatc    660
aatgacgccg tcgtggtaga caacaccggc cgctggcgtg accgcgaagg cctgtcccag    720
cacctcaagt ccaagggcgt tgccaaggtt gtactcaccg cgccgggcaa gggcgatctg    780
aagaacatcg tgtacggcat caaccacacc gacatcaccg cagatgatca gatcgtttcc    840
gcagcatcat gcaccaccaa tgccattacc ccagtgctca aggtgatcaa tgatcgctac    900
ggcgtggaat tcggccacgt agaaaccgtt cactccttca ccaatgacca gaacctgatc    960
gacaacttcc acaagggttc tcgccgtggt cgcgcagcag gtctgaatat ggttctcacc   1020
gaaaccggcg ctgcaaaggc tgtatccaag gcgcttccag agctggaagg caagctcacc   1080
ggcaatgcca tccgcgttcc taccccgac gtgtccatgg ctgtgctcaa cttgaccctg   1140
aacacggagg tggaccgcga tgaggtcaac gagttcctcc gccgtgtgtc cctgcactct   1200
gacttgcgcc agcaaatcga ctggatccgt tccccagagg ttgtttccac tgacttcgtg   1260
ggcaccaccc acgcgggcat cgttgatggt ctagccacca tcgcaaccgg tcgccacctg   1320
gtgctttacg tgtggtacga caacgagttc ggctactcca accaggtcat tcgcatcgtc   1380
gaggagatcg ccggcgtgcg tcctcgcgtg tacccggagc gcaggcagcc agccgtacta   1440
tag                                                                 1443

<210> SEQ ID NO 64
<211> LENGTH: 1005
<212> TYPE: DNA
<213> ORGANISM: Artificial Sequence
<220> FEATURE:
<223> OTHER INFORMATION: NCgl1526

<400> SEQUENCE: 64
atgaccattc gtgttggtat taacggattt ggccgtatcg gacgtaactt cttccgcgca     60
gttctggagc gcagcgacga tctcgaggta gttgcagtca acgacctcac cgacaacaag    120 acccttttcca cccttctcaa gttcgactcc atcatgggcc gccttggcca ggaagttgaa    180
tacgacgatg actccatcac cgttggtggc aagcgcatcg ctgtttacgc agagcgcgat    240
ccaaagaacc tggactgggc tgcacacaac gttgacatcg tgatcgagtc caccggcttc    300
ttcaccgatg caaacgcggc taaggctcac atcgaagcag gtgccaagaa ggtcatcatc    360
tccgcaccag caagcaacga agacgcaacc ttcgtttacg gtgtgaacca cgagtcctac    420
gatcctgaga ccacaacgt gatctccggc gcatcttgca ccaccaactg cctcgcacca    480
atggcaaagg tcctaaacga caagttcggc atcgagaacg gcctcatgac caccgttcac    540
gcatacactg gcgaccagcg cctgcacgat gcacctcacc gcgacctgcg tcgtgcacgt    600
gcagcagcag tcaacatcgt tcctacctcc accggtgcag ctaaggctgt tgctctggtt    660
ctcccagagc tcaagggcaa gcttgacggc tacgcacttc gcgttccagt tatcaccggt    720
tccgcaaccg acctgaccct caacaccaag tctgaggtca ccgttgagtc catcaacgct    780
gcaatcaagg aagctgcagt cggcgagttc ggcgagaccc tggcttactc cgaagagcca    840
ctggtttcca ccgacatcgt ccacgattcc cacggctcca tcttcgacgc tggcctgacc    900
aaggtctccg gcaacaccgt caaggttgtt tcctggtacg acaacgagtg gggctacacc    960
```
tgccagctcc tgcgtctgac cgagctcgta gcttccaagc tctaa      1005

<210> SEQ ID NO 65
<211> LENGTH: 1299
<212> TYPE: DNA
<213> ORGANISM: Artificial Sequence
<220> FEATURE:
<223> OTHER INFORMATION: NCgl2272

<400> SEQUENCE: 65
atgagttcaa cgaccctaac tgatgaccaa attcgcgaca tgagcggac cgaagttcta      60
gctaaagcaa ctgcagctaa aacatcgtc ccggatattg cagtgttggg caccggaccg     120
aagaacgcaa tcctgcgtgc ggcggcagat gaactcgttg cacgcagcgc agaaatcatc     180
gaagccaacg cttccgatat cgaagcgggt cgcgcaaacg gcatggaaga tccatgatt     240
gatcgccttg cccttgatga atctcgcatt gagggcatcg ctggcggttt cgccaggtt      300
gctggcctga ccgacccagt gggtgaagta ctgcgcggac atgtcatgga aaacggcatt     360
cagatgaagc aggtccgtgt gcctttgggc gtgatgggca tggtctatga gcccgccct      420
aacgtcaccg tcgacgcctt cggcctggca ctcaagtccg aaacgtagc tttgctgcgc      480
ggttcctcca cagctgtgca ttccaacacc aagctcgtgg aaatcctgca ggacgtcctc     540
gagcgtttcg agctgccacg cgaaaccgtg cagttgctgc cttgccaaac ccgcggatcc     600
gtccaagatt tgatcaccgc acgcggcctc gttgacgtgg tcatcccacg cggcggcgca     660
ggactaatca acgcagtggt caccggtgcg accgtgccca ccattgaaac cggcaccggc     720
aactgccact tctacatcga tgccgaagcc aagcttgatc aggcaatcgc catggtcatc     780
aacggcaaga cccgccgctg cagcgtgtgc aacgctactg aaaccgcgct ctctcgacgcc      840
gccctcagcg actcagacaa gcttgcagtc gtccaggcgc tccaggaagc aggagtcaca     900
attcatggac gggtggccga attggaagca ttcggtgcaa ccgacgtggt ggaagcaact     960
gaaactgact gggattctga gtacctgtcc ttcgatatcg ctgtcgctgt ggttgacggt    1020
gtggatggag ctctggcaca catcgctaag tacagcacca agcacaccga agcgatcgcc    1080
acccaaaaca ttgaaaccgc tcagcgcttt gcagatcgcg tcgatgcagc agcggtgatg    1140
ataaacgcat ccaccgccta caccgatggg gagcagtacg gcatgggcgc ggagatcggc    1200
atttccaccc agaaactgca tgcacgtgga ccaatggccc tgccagagct gacctccacc    1260
aagtggattc tgcagggcac aggacaaatt aggccttaa                             1299

<210> SEQ ID NO 66
<211> LENGTH: 1455
<212> TYPE: DNA
<213> ORGANISM: Artificial Sequence
<220> FEATURE:
<223> OTHER INFORMATION: NCgl2578

<400> SEQUENCE: 66
gtgactgcaa catttgctgg aatcgacgcc accaaacacc tcatcggagg tcagtgggtg      60
gagggaaact cggatcgaat ttccaccaat atcaatcctt acgacgattc cgtaatcgcc     120
gaaagcaaac aagcttccat tgctgatgtt gatgccgcgt atgaagccgc gaagaaggcc     180
caggctgagt gggcagctac gcccgctgcg aacgatctg ccatcatcta ccgtgcggct      240
gaacttcttg aagagcaccg ggaggaaatc gtggaatggc tgatcaagga atccggctcg     300
acgcgttcca aggctaattt ggaaatcact ttggcaggaa acatcactaa agaatcggct     360

```
tcattccctg gtcgtgtgca tggtcgaatt tctccttcga atactccggg caaagaaaac    420
cgtgtgtacc gcgtagccaa gggcgttgtc ggagtgatta gtccatggaa tttcccactg    480
aacctctcga tccgctcggt tgctccggca ctagccgtgg gcaacgccgt agtgattaag    540
cctgcgagtg ataccccagt tactggtggt gtaattcctg cacgaatctt tgaggaggcc    600
ggagttcctg caggcgtgat cagcacggtt gcgggcgcag atctgaaat cggtgatcac     660
tttgtcaccc acgccgtgcc aaagctgatt tctttcaccg gttcaacccc agtcggtcgt    720
cgtgtcggtg agctggcaat taatggtgga ccaatgaaaa ctgttgcact agagctcggt    780
ggcaacgcgc cgttcgttgt gcttgccgac gccgacatcg acgccgctgc ccaggctgcc    840
gcagttggcg ctttcctaca ccagggacag atttgtatgt caatcaaccg agtcattgtt    900
gatgctgcag ttcatgatga attcctagag aagttcgttg aagcagtgaa gaacattcca    960
accggcgatc aagcgcaga aggaaccctt gttggacctg tcattaatga cagtcagctc    1020
agtggtttga aggaaaagat cgagttggcc aaaaaggaag gcgcaaccgt ccaggttgaa    1080
gggccaattg aaggccgact ggttcatccg catgtgttct ctgatgtcac ctctgacatg    1140
gaaatcgctc gtgaggaaat cttcggacct ctcatcagcg tgctgaaggc cgatgatgag    1200
gcacacgcag cagagctggc caatgcttcc gactttggtt tgagcgcggc agtgtggtcg    1260
aaggatattg atcgtgcagc ccagtttgct ctgcagattg attccggcat ggttcacatc    1320
aatgacctca ccgtcaacga tgaaccacac gtgatgttcg gtggttcaaa gaactctggc    1380
ctcggccgct tcaacggcga ttgggcgatc gaggagttca ccacagatcg atggatcggc    1440
atcaagcgca gctaa                                                    1455

<210> SEQ ID NO 67
<211> LENGTH: 1566
<212> TYPE: DNA
<213> ORGANISM: Artificial Sequence
<220> FEATURE:
<223> OTHER INFORMATION: NCgl2619

<400> SEQUENCE: 67
atgatcaaac gtcttccttt aggtccgctg cctaaagaac ttcatcagac tctgcttgat     60
ctgaccgcaa atgcccaaga tgcggcgaaa gtggaggtta tagcgccatt tactggcgag    120
accctcggat tgttttttga tggtgatgag caagacgtcg agcatgcttt tgcactttca    180
agggcagccc agaaaaagtg ggtgcacacc acggcagtgg aacggaagaa gatcttcctg    240
aagtttcatg atctggtatt gaaaaaccgt gagctgctca tggacatcgt gcagttggaa    300
acaggcaaaa atcgagcatc ggctgccgat gaggtgttgg acgttgcgat caccacccgc    360
ttctacgcaa acaatgcagg aaagttttta aatgacaaga aacgccccgg cgcgcttccg    420
atcatcacga aaacacaca acagtatgtg cccaagggag tggtcgggca gatcacgccg    480
tggaattacc ctttaacttt gggagtatct gatgctgttc cggcgctgct ggcaggaaac    540
gcagtggtgg ctaaacctga cctcgcgaca cctttctcct gcttgatcat ggtgcacctg    600
ctcattgaag ccggtctgcc gcgtgatttg atgcaggttg tcaccggccc tggcgatatt    660
gttggcggtg cgattgcagc tcagtgtgat ttcctcatgt tcactggatc cacggccacg    720
ggccggatct tgggtcggac aatgggtgag cgtttggtgg gtttctctgc ggaattaggc    780
ggaaagaacc ctcttattgt ggccaaggat gcagatctgg acaaggtgga agctgagctt    840
ccgcaggcgt gttttttccaa ctcggggcaa ttgtgtgtct ccactgaacg tatttatgtc    900
gaggaagacg tgtacgagga ggtgattgca cggtttagca aggcggcgaa agccatgtcc    960
```

```
attggtgccg gatttgagtg gaaatatgag atgggttcgt tgatcaatca ggcgcagctg      1020
gatcgggtga gcacctttgt tgatcaggct aaagctgcgg gcgccacggt gctgtgcggt      1080
ggcaagtcac gccctgatat tggtcccttc ttctatgagc ccacggtatt ggcggatgtc      1140
ccagagggca ccccactgct cacggaggaa gtcttcgggc cggtggtgtt catcgaaaag      1200
gtagccacac tggaagaagc cgtcgataag gcaaatggca cgccctacgg cctgaatgcg      1260
tccgtctttg ggtcgtcgga aaccggcaat cttgttgcag ccagctgga agctggcggt       1320 atcggtatta tgatggcta cgccgcgacg tgggcgagcg tgtccacgcc tctgggtggc       1380
atgaagcagt cggggctggg gcaccgccat ggtgcgaggg gaattacaaa atatgcggag      1440
atccgaaaca tcgcggagca gcgctggatg tctatgcgtg ggccggccaa atgccgcga       1500 aaggtgtact cagacaccgt ggccacagcg ctaaagctgg gcaaaatctt taaagttttg      1560
ccgtag                                                                 1566
```

<210> SEQ ID NO 68  
<211> LENGTH: 1521  
<212> TYPE: DNA  
<213> ORGANISM: Artificial Sequence  
<220> FEATURE:  
<223> OTHER INFORMATION: NCgl2698

<400> SEQUENCE: 68

```
atgactgtct acgcaaatcc aggaaccgaa ggctcgatcg ttaactatga aaagcgctac      60
gagaactaca ttggtggcaa gtgggttcca ccggtagagg gccagtacct tgagaacatt      120
tcacctgtca ctggtgaagt tttctgtgag gtcgcacgtg gcaccgcagc ggacgtggag      180
cttgcactgg atgctgcaca tgcagccgct gatgcgtggg gcaagacttc tgtcgctgaa      240
cgtgctctga tcctgcaccg cattgcggac cgcatggaag agcacctgga gaaaatcgca      300
gttgcagaaa cctgggagaa cggcaaggca gtccgtgaga ctcttgctgc agatatccca      360
ctggcaatcg accacttccg ctactttgct ggcgcgatcc gtgctcagga agatcgttcc      420
tcacagatcg accacaacac tgttgcttac cacttcaacg agccaatcgg tgttgttggt      480
cagatcattc cttggaactt cccaatcctc atggctacct ggaagctcgc accggcactt      540
gctgcaggta acgcgatcgt catgaagcca gctgagcaga ccccagcatc cattttgtat      600
ctgattaaca tcatcggcga tctcatccca gagggcgtcc tcaacatcgt caacggactc      660
ggcggtgaag caggcgctgc actgtccggc tctaatcgga ttggcaagat tgctttcacc      720
ggttccaccg aggtcggcaa gctgatcaac cgcgctgcat ccgacaagat cattcctgtc      780
accctggagc tcggcggtaa gtccccatcc atcttcttct ccgatgttct gtcacaggat      840
gacgccttcg cagagaaggc agttgaaggc ttcgcgatgt tcgccctcaa tcagggtgaa      900
gtttgtacct gtccttcccg tgcacttgtt catgagtcca tcgctgatga attcctcgag      960
cttggcgtga agcgagttca gaacatcaag ctgggtaacc cacttgatac tgaaaccatg      1020
atgggtgctc aggcgtccca ggagcagatg gacaagatct cctcctacct gaagatcggc      1080
ccagaagaag cgctcaaac cctcactggt ggcaaggtca acaaggttga tggcatggag      1140
aacggttact acattgagcc aaccgttttc gcgggcacca cgacatgag gatcttccgc      1200 gaggaaatct tcggaccagt cctttctgtt gctaccttca gcgacttcga tgaggccatc      1260
cgtattgcaa acgacaccaa ctacggcctc ggcgctggtg tctggagccg tgaccaaaac      1320
accatttatc gtgtcaggtcg cgcaatccag gctggtcgag tttgggtcaa ccagtaccac      1380
```

| | | | | |
|---|---|---|---|---|
| aactacccag | cgcactccgc | tttcggtgga | tacaaggagt | ccggcatcgg ccgtgagaac | 1440 |
| cacctcatga | tgctgaacca | ctaccagcag | accaagaacc | tgttggtctc ctacgatcca | 1500 |
| aacccaaccg | gactgttctg | a | | | 1521 |

RECOMBINANT CORYNEBACTERIUM HAVING 1,3-PDO PRODUCTIVITY AND REDUCED 3-HP PRODUCTIVITY, AND METHOD FOR PRODUCING 1,3-PDO BY USING SAME

CROSS-REFERENCE TO RELATED APPLICATIONS

This application is a U.S. national phase under the provisions of 35 U.S.C. § 371 of International Patent Application No. PCT/KR19/04961 filed Apr. 24, 2019, which in turn claims priority under 35 U.S.C. § 119 of Korean Patent Application No. 10-2018-0058952 filed May 24, 2018. The disclosures of such international patent application and Korean priority patent application are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "537_SeqListing_ST25.txt" created on Nov. 16, 2020 and is 54,316 bytes in size. The sequence listing contained in this .txt file is part of the specification and is hereby incorporated by reference herein in its entirety.

TECHNICAL FIELD

The present invention relates to a recombinant *Corynebacterium* having 1,3-PDO (1,3-propanediol) production ability and reduced (inhibited) 3-HP production ability, and a method for producing 1,3-PDO using the same, and more particularly, to a mutant microorganism having deleted or attenuated 3-HP production ability and producing 1,3-PDO from glycerol, wherein the mutant microorganism is produced by introducing a gene encoding a glycerol facilitator, a gene encoding glycerol kinase, a gene encoding glycerol dehydrogenase, a gene encoding glycerol dehydratase, a gene encoding glycerol reactivase and a gene encoding 1,3-PDO oxidoreductase into *Corynebacterium glutamicum*, and deleting or attenuating a gene encoding aldehyde dehydrogenase from the *Corynebacterium glutamicum*.

BACKGROUND ART 1,3-propanediol (1,3-PDO) is a chemical substance used as a monomer for the synthesis of polymers such as polyether, polyurethane and polytrimethylene terephthalate (PTT). Conventional methods mainly used for producing 1,3-PDO are chemical synthesis methods, and hydration of acrolein, hydroformylation of ethylene oxide in the presence of phosphine, or enzymatic conversion of glycerol may be used. These chemical production methods have limitations because they include high-cost and environmentally hazardous production processes (Lee et al., *Renewable and Sustainable Energy Reviews*, 42 (Supplement C): 963-972; U.S. Pat. No. 8,236,994 B2).

A biological method of producing 1,3-PDO using microorganisms is mainly performed using microorganisms such as *Klebsiella*, *Clostridia*, *Enterobacter*, *Citrobacter*, and *Lactobacilli*. In all of these methods, glycerol is directly converted to 1,3-PDO through two successive metabolic pathways of converting glycerol to 3-hydroxyproprionaldehyde (3-HPA) using glycerol dehydratase and then reducing the 3-HPA to 1,3-PDO using 1,3-PDO oxidoreductase (FIG. 1). DuPont Inc. has already successfully commercialized 1,3-PDO by introducing the metabolic pathway into *E. coli*. However, there are disadvantages in which most microorganisms including *Escherichia coli* used for biosynthesis of 1,3-PDO are produced along with various byproducts, such as formate, acetate, lactate, ethanol, and 2,3-butanediol.

*Corynebacterium glutamicum* is a Gram-positive anaerobic bacterium which is widely used in fermentation processes for amino acid production. In addition, in order to produce various kinds of chemical substances and fuels using *Corynebacterium glutamicum*, a great deal of metabolic engineering research has been performed with the goal of realizing consumption of various types of carbon sources such as glucose and xylose, but there are few studies on the production of 1,3-PDO, and studies have reported simultaneous production of glutamic acid by promoting cell growth with glucose and producing 1,3-PDO with glycerol using glucose and glycerol as carbon sources in *Corynebacterium glutamicum* (Huang et al., *Scientific Reports*, 7: 42246, 2017).

However, 3-hydroxypropionaldehyde (3-HPA), which is an intermediate in the 1,3-PDO biosynthetic metabolic pathway, has a toxic effect when accumulated in cells, and acts as a precursor of 3-hydroxypropionic acid, which is one of the byproducts of 1,3-PDO. 3-HP is converted from 3-HPA through an aldehyde dehydrogenase enzyme, which has already been reported in the research to produce 3-HP by overexpressing GabD4(E209Q/E269Q), a mutant enzyme of GabD4, the gene encoding aldehyde dehydrogenase derived from *Cupriavidus necator*, in *Corynebacterium glutamicum* (Chen et al., *Metabolic Engineering*, 39:151, 2017). However, this is an effect caused by the overexpression of foreign enzymes, and there is no report associated with a gene that specifically accepts 3-HPA as a substrate, among aldehyde dehydrogenases that are still naturally present in *Corynebacterium glutamicum*, and that is involved in 3-HP biosynthesis.

Accordingly, as a result of extensive efforts to more efficiently produce 1,3-PDO through a biological pathway, the present inventors have found that 3-HP production ability was inhibited and thus 1,3-PDO was efficiently produced when culturing *Corynebacterium glutamicum* that was imparted with 1,3-PDO production ability by introducing a gene encoding glycerol dehydrogenase, a gene encoding glycerol dehydratase, a gene encoding glycerol reactivase and a gene encoding 1,3-PDO oxidoreductase, and at the same time, in which 3-HPA production ability is inhibited by deleting candidate aldehyde dehydrogenase genes present in *Corynebacterium glutamicum*, in order to produce a mutant *Corynebacterium glutamicum* having 1,3-PDO production ability and from which 3-HP production ability is inhibited or deleted. Based on this finding, the present invention was completed.

DISCLOSURE

Therefore, the present invention has been made in view of the above problems, and it is one object of the present invention to provide a mutant *Corynebacterium glutamicum* capable of efficiently producing 1,3-PDO due to inhibited 3-HP production ability.

It is another object of the present invention to provide a method of producing 1,3-PDO by culturing the mutant *Corynebacterium glutamicum*.

In accordance with one aspect of the present invention, the above and other objects can be accomplished by the provision of a mutant microorganism having deleted or attenuated 3-HP production ability and producing 1,3-PDO from glycerol, in which (i) a gene encoding a glycerol facilitator, (ii) a gene encoding glycerol kinase and a gene encoding glycerol dehydrogenase, (iii) a gene encoding glycerol dehydratase, (iv) a gene encoding glycerol reactivase and (v) a gene encoding 1,3-PDO oxidoreductase are introduced into *Corynebacterium glutamicum*, and a gene encoding aldehyde dehydrogenase is deleted or attenuated from the *Corynebacterium glutamicum*.

In accordance with another aspect of the present invention, there is provided a method of producing 1,3-PDO from glycerol, including (a) culturing the mutant microorganism in a glycerol-containing medium to produce 1,3-PDO, and (b) collecting the produced 1,3-PDO.

DESCRIPTION OF DRAWINGS

FIG. 1 is a schematic diagram illustrating the overall metabolic pathway of the mutant *Corynebacterium glutamicum* according to the present invention, including a 1,3-PDO biosynthetic metabolic pathway, a 3-HP biosynthetic metabolic pathway and a glycerol decomposition metabolic pathway.

FIG. 2 shows a pCSglpFKD recombinant vector into which glpF, glpK and glpD genes encoding the glycerol degradation metabolic pathway are inserted.

FIG. 3 shows a pCG-9ts-ALD1 recombinant vector produced to delete the NCgl0049 gene, among 13 aldehyde dehydrogenase candidates.

FIG. 4 shows a pEK-pdu recombinant vector produced by inserting the pduCDEGH gene cluster encoding glycerol dehydratase in order to construct a 3-HPA biosynthetic metabolic pathway.

FIG. 5 shows a pEK-pduyE recombinant vector produced by inserting the yqhD gene encoding *E. coli* 1,3-PDO oxidoreductase into the pEK-pdu vector in order to construct a 1,3-PDO biosynthetic metabolic pathway.

FIG. 6 shows the results of 3-HP production when using glycerol as a single carbon source by introducing pCSglpFKD and pEK-pduyE vectors into *Corynebacterium glutamicum* strains from which 11 types of aldehyde dehydrogenase are deleted.

FIG. 7 shows the results of 1,3-PDO production when using glycerol as a single carbon source by introducing pCSglpFKD and pEK-pduyE vectors into *Corynebacterium glutamicum* strains from which 11 aldehyde dehydrogenases are deleted.

BEST MODE

Unless defined otherwise, all technical and scientific terms used herein have the same meanings as appreciated by those skilled in the field to which the present invention pertains. In general, the nomenclature used herein is well-known in the art and is ordinarily used.

In the present invention, a mutant *Corynebacterium glutamicum* having increased 1,3-PDO production ability was produced by inhibiting the production ability of 3-HP converted from the same precursor as 3-HPA, which is a precursor of 1,3-PDO, in the mutant *Corynebacterium glutamicum* in order to improve the 1,3-PDO yield using the mutant *Corynebacterium glutamicum* having 1,3-PDO production ability.

In the present invention, the mutant *Corynebacterium glutamicum* having 1,3-PDO production ability was produced by introducing a gene encoding glycerol dehydrogenase, a gene encoding glycerol dehydratase, a gene encoding glycerol reactivase and a gene encoding 1,3-PDO oxidoreductase into *Corynebacterium glutamicum*, which does not naturally have 1,3-PDO production ability.

The gene encoding glycerol dehydratase, the gene encoding glycerol reactivase and the gene encoding 1,3-PDO oxidoreductase used in the present invention are *Klebsiella pneumoniae*-derived pduCDEGH and *E. coli*-derived yqhD, and the 1,3-PDO production ability was determined after introducing the genes into *Corynebacterium glutamicum*.

*Corynebacterium glutamicum* used in the present invention is a microorganism that naturally allows for glycerol diffusion, but does not allow for cell growth when using a single carbon source. For this reason, *Corynebacterium glutamicum* enabling cell growth from a glycerol carbon source was produced by introducing a gene encoding a glycerol facilitator, a gene encoding glycerol kinase, and a gene encoding glycerol dehydrogenase.

In the present invention, glpF, glpK, and glpD derived from *E. coli* were respectively introduced as the gene encoding glycerol facilitator, the gene encoding glycerol kinase, and the gene encoding glycerol dehydrogenase.

In the present invention, *Corynebacterium glutamicum* introduced with the 1,3-PDO biosynthetic metabolic pathway produces 3-HP (3-hydroxypropionic acid) as a main byproduct in addition to 1,3-PDO, and 3-HP is converted from 3-HPA (3-hydroxypropionaldehyde), which is the same precursor as 3-PDO, by an aldehyde dehydrogenase enzyme. Enzymes that specifically react strongly to 3-HPA were identified from candidate enzymes of aldehyde dehydrogenases present in *Corynebacterium glutamicum*, and the effects obtained through in-vivo culture were determined.

Thus, in one aspect, the present invention is directed to a mutant microorganism having deleted or attenuated 3-HP production ability and producing 1,3-PDO from glycerol, wherein the mutant microorganism is produced by introducing (i) a gene encoding a glycerol facilitator, (ii) a gene encoding glycerol kinase and a gene encoding glycerol dehydrogenase, (iii) a gene encoding glycerol dehydratase, (iv) a gene encoding glycerol reactivase and (v) a gene encoding 1,3-PDO oxidoreductase into *Corynebacterium glutamicum*, and deleting or attenuating a gene encoding aldehyde dehydrogenase from the *Corynebacterium glutamicum*.

In the present invention, the gene encoding aldehyde dehydrogenase, which is an enzyme involved in providing the mutant *Corynebacterium glutamicum* having inhibited 3-HP production ability, includes 11 candidate genes present in *Corynebacterium glutamicum*, namely NCgl0049, NCgl0157, Ncgl0437, NCgl0463, NCgl0521, NCgl0523, NCgl0900, NCgl2272, NCgl2578, NCgl2619, and NCgl2698.

In the present invention, a change in 3-HP production due to deletion of the 11 candidate genes selected for 3-HP biosynthesis inhibition was determined, and a mutant *Corynebacterium glutamicum* having increased 1,3-PDO production was produced.

In the present invention, at least one of the genes encoding aldehyde dehydrogenase may be deleted or attenuated.

In the present invention, the gene encoding the glycerol facilitator, the gene encoding glycerol kinase, and the gene encoding glycerol dehydrogenase may be glpF, glpK and glpD, respectively, and the gene encoding glycerol dehydratase, the gene encoding glycerol reactivase, and the gene encoding 1,3-PDO oxidoreductase may be pduCDEG or yqhD.

In the present invention, the introduced genes may be overexpressed by a strong promoter selected from the group consisting of tac, trc and tuf.

As used herein, the term "intrinsic activity" refers to the activity of an enzyme that a microorganism innately has in an unmodified state, the expression "modified to have enhanced activity compared to intrinsic activity" means that an activity is newly introduced or improved compared to the enzymatic activity before modification.

As used herein, the term "enhancement in enzymatic activity" includes not only having effects beyond original functions through new introduction of activity of enzymes or improvement thereof, but also increased enzymatic activity based on an increase in endogenous gene activity, amplification of endogenous genes due to internal or external factors, deletion of inhibitory regulatory factors of the gene expression, an increase in the number of copies of genes, introduction of genes from external sources, modification of expression regulation sequences, in particular, promoter replacement or modification, and increased enzymatic activity due to gene mutations.

As used herein, the term "modified to have enhanced activity compared to intrinsic activity" means a state in which the activity of the microorganism after manipulation is increased compared to the activity of the microorganism before manipulation, such as the introduction of genes exhibiting activity or an increased number of copies of the corresponding gene, and deletion of inhibitory regulatory factors of gene expression or modification of expression regulation sequences, for example, the use of enhanced promoters.

As used herein, the term "deletion" encompasses cases in which a gene is not expressed through a method of mutation, replacement or deletion of a part or the entirety of the base of the gene and cases in which the enzymatic activity thereof is not expressed even though the gene is expressed, and includes all operations for blocking biosynthetic pathways that the enzyme of the corresponding gene mediates.

As used herein, the term "overexpression" refers to expression at a level higher than the level at which the corresponding gene in the cell is expressed in a normal state, and includes increases in expression levels by replacing promoters of genes present on the genome with stronger promoters or cloning the corresponding gene into the expression vector to transform cells therewith.

As used herein, the term "vector" means a DNA product containing a base sequence of a polynucleotide encoding a target protein operably linked to a suitable control sequence so as to express the target protein in a suitable host. The control sequence includes a promoter capable of initiating transcription, any operator sequence for controlling such transcription, a sequence encoding a suitable mRNA ribosomal binding site, and a sequence for controlling termination of transcription and translation. After the vector is transformed into a suitable host cell, it may be replicated or perform functions independent of the host genome, and may be integrated with the genome.

Since the plasmid is the most commonly used type of vector, the terms "plasmid" and "vector" may be used interchangeably throughout the specification of the present invention. For the purpose of the present invention, a plasmid vector is preferably used. A typical plasmid vector that can be used for this purpose includes (a) a replication origin to efficiently conduct replication such that several hundred plasmid vectors are included in each host cell, (b) an antibiotic resistance gene to screen a host cell transformed with the plasmid vector, and (c) a restriction enzyme cleavage site into which a foreign DNA fragment is inserted. Even if an appropriate restriction enzyme cleavage site is not present, the vector and foreign DNA can be easily ligated using a synthetic oligonucleotide adapter or a linker according to a conventional method.

After ligation, the vector should be transformed into an appropriate host cell. The host cells preferred in the present invention are prokaryotic cells. Suitable prokaryotic host cells include *E. coli* DH5a, *E. coli* JM101, *E. coli* K12, *E. coli* W3110, *E. coli* X1776, *E. coli* XL-1 Blue (Stratagene), *E. coli* B, *E. coli* B21 and the like. However, *E. coli* strains such as FMB101, NM522, NM538 and NM539, as well as other prokaryotic species and genera, and the like, can also be used. In addition to the *E. coli* mentioned above, strains of the genus *Agrobacterium*, such as *Agrobacterium* A4, *Bacillus* strains such as *Bacillus subtilis*, other enterobacteria such as *Salmonella typhimurium* or *Serratia marcescens*, and various strains of the genus *Pseudomonas* can be used as host cells.

Transformation of prokaryotic cells can be easily carried out using a calcium chloride method described in Section 1.82 of Sambrook et al., supra. Alternatively, electroporation (Neumann, et al., EMBO J., 1: 841, 1982) can be used for transformation of these cells.

The vector used for overexpression of the gene according to the present invention may be any expression vector known in the art, and is preferably a pET-based vector (Novagen). When cloning is performed using the pET-based vector, histidine groups are bonded to the ends of the expressed protein, so that the protein can be effectively purified. The expressed protein can be isolated from the cloned gene through a general method known in the art, and can be specifically isolated using a chromatographic method using Ni-NTA His-conjugated resin (Novagen). In the present invention, the recombinant vector may be pET-SLTI66, and the host cell may be *E. coli* or *Agrobacterium*.

As used herein, the term "expression control sequence" means a DNA sequence essential for the expression of a coding sequence operably linked to a particular host organism. Such a control sequence includes promoters for conducting transcription, any operator sequences for controlling such transcription, sequences for encoding suitable mRNA ribosome-binding sites, and sequences for controlling the termination of transcription and translation. For example, control sequences suitable for prokaryotes include promoters, optionally operator sequences and ribosome-binding sites. Control sequences suitable for eukaryotic cells include promoters, polyadenylation signals, and enhancers. The factor that has the greatest impact on the expression level of a gene in a plasmid is the promoter. SRα promoters, cytomegalovirus-derived promoters and the like are preferably used as promoters for high expression. Any of a wide variety of expression control sequences may be used for the vector in order to express the DNA sequences of the present invention. Useful expression control sequences include, for example, early and late promoters of SV40 or adenovirus, the lac system, the trp system, the TAC or TRC system, T3 and T7 promoters, the major operator and promoter regions of phage lambda, control regions of fd code proteins, promoters of 3-phosphoglycerate kinase or other glycol lyases, promoters of the phosphatase, such as Pho5, promoters of yeast alpha-mating systems and other sequences known to control gene expression of prokaryotic or eukaryotic cells or viruses and various combinations thereof. The T7 promoter may be useful for expressing proteins of the present invention in *E. coli*.

When a nucleic acid sequence is aligned with another nucleic acid sequence based on a functional relationship, it is "operably linked" thereto. This may be gene(s) and control sequence(s) linked in such a way so as to enable gene expression when a suitable molecule (e.g., a transcriptional activator protein) is linked to the control sequence(s). For example, DNA for a pre-sequence or secretory leader is operably linked to DNA for a polypeptide, when expressed as a pre-protein involved in the secretion of the polypeptide; a promoter or enhancer is operably linked to a coding sequence when it affects the transcription of the sequence; or a ribosome-binding site is operably linked to a coding sequence when it affects the transcription of the sequence; or the ribosome-binding site is operably linked to a coding sequence when positioned to facilitate translation. Generally, "operably linked" means that the linked DNA sequence is in contact therewith, and a secretory leader is in contact therewith and is present in the reading frame. However, the enhancer need not be in contact therewith. The linkage of these sequences is carried out by ligation (linkage) at convenient restriction enzyme sites. When no such site exists, a synthetic oligonucleotide adapter or a linker according to a conventional method is used.

As used herein, the term "expression vector" commonly refers to a recombinant carrier, into which a fragment of heterologous DNA is inserted, and generally means a fragment of double-stranded DNA. Herein, the heterologous DNA is xenogenous DNA that is not naturally found in the host cell. Once an expression vector is present in a host cell, it can replicate independently of the host chromosomal DNA, and several copies of the vector and inserted (heterologous) DNA thereof can be produced.

As is well known in the art, in order to increase the expression level of a transgene in a host cell, the gene should be operably linked to transcriptional and translational expression control sequences that function in a selected expression host. Preferably, the expression control sequence and the corresponding gene are included in one expression vector containing both a bacterial selection marker and a replication origin. When the expression host is a eukaryotic cell, the expression vector should further include a useful expression marker in the eukaryotic expression host.

The host cell transfected or transformed with the expression vector described above constitutes another aspect of the present invention. As used herein, the term "transfection" means introducing DNA into a host and making the DNA replicable using an extrachromosomal factor or chromosomal integration. As used herein, the term "transformation" means that an expression vector is accommodated in the host cell, regardless of whether or not any coding sequence is actually expressed.

It should be understood that not all vectors and expression control sequences function identically in expressing the DNA sequences of the present invention. Likewise, not all hosts function identically for the same expression system. However, those skilled in the art will be able to make appropriate selection from among a variety of vectors, expression control sequences and hosts without excessive burden of experimentation and without departing from the scope of the present invention. For example, selection of a vector should be carried out in consideration of a host because the vector should be replicated therein. The number of replications of the vector, the ability to control the number of replications, and the expression of other proteins encoded by the corresponding vector, such as the expression of antibiotic markers, should also be considered. In selecting the expression control sequence, a number of factors should be considered. For example, the relative strength of the sequence, controllability, and compatibility with the DNA sequences of the present invention should be considered, particularly in relation to possible secondary structures. The single-cell host may be selected in consideration of factors such as the selected vector, the toxicity of the product encoded by the DNA sequence of the present invention, secretion characteristics, the ability to accurately fold proteins, culture and fermentation factors, and ease of purification of the product encoded by the DNA sequence according to the present invention from the host. Within the scope of these factors, those skilled in the art can select various vector/expression control sequences/host combinations capable of expressing the DNA sequences of the present invention in fermentation or large animal cultures. As a screening method for cloning cDNA of proteins through expression cloning, a binding method, a panning method, a film emulsion method or the like can be applied.

Hereinafter, the present invention will be described in more detail with reference to examples. However, it will be obvious to those skilled in the art that these examples are provided only for illustration of the present invention and should not be construed as limiting the scope of the present invention.

In the following Examples, only genes derived from a specific strain are given as examples of genes to be introduced, but it will be apparent to those skilled in the art that any genes may be used without limitation, as long as they are expressed in host cells into which they are to be introduced and exhibit the same activity.

Example 1: Production of pCSglpFKD Vector for Production of Mutant *Corynebacterium glutamicum* Capable of Growing Using Glycerol as Single Carbon Source 1-1: Production of pCSglpFKD Vector for Constructing Glycerol Decomposition Metabolic Pathway

*Corynebacterium glutamicum* is known to be unable to grow cells using glycerol as a single carbon source. Therefore, in order to construct the glycerol decomposition metabolic pathway, the gene encoding the enzyme derived from *E. coli* W3110 and responsible for the glycerol decomposition metabolic pathway was first expressed using the *Corynebacterium glutamicum* shuttle vector, pCES208s-H36-S3.

PCR was performed using the chromosomal DNA of *E. coli* W3110 (ATCC 39936) as a template and primers of SEQ ID NOS: 1 and 2 to obtain glpFK gene fragments encoding glycerol facilitator and glycerol kinase operon enzymes, and PCR was performed using primers of SEQ ID NOS: 3 and to obtain glpD gene fragments encoding glycerol-3-phosphate dehydrogenase. In order to ligate the glpFK gene fragment with the glpD gene fragment, overlapping PCR was performed using the primers of SEQ ID NOS: 1 and 4 to produce a glpFKD gene fragment (SEQ ID NO: 53). In order to linearize the pCES208s-H36-S3 vector ((the vector (SEQ ID NO: 21) obtained by replacing the Km antibiotic of pCES208-H36 vector (Korean Patent Laid-open Publication No. 10-2013-0022691, or Yim S. S. et al., *Biotechnol. Bioeng.*, 110:2959, 2013, SEQ ID NO: 54)) with the antibiotic spectinomycin, PCR was performed using primers of SEQ ID NOS: 5 and 6, and a pCSglpFKD vector was constructed using the produced glpFKD gene fragment and a Gibson assembly method (FIG. 2).

TABLE 1

Primers for producing pCSglpFKD vector

| SEQ ID NO | Nucleotide sequence |
|---|---|
| SEQ ID NO: 1 | 5'-TTGGTTGGTAGGAGTAGCATGGGATCCATGAGTCAAACATCAACCTT-3' |
| SEQ ID NO: 2 | 5'-GTTTCCATCTATATCTCCTTTTATTCGTCGTGTTCTTCCC-3' |
| SEQ ID NO: 3 | 5'-AAGGAGATATAGATGGAAACCAAAGATCTGAT-3" |
| SEQ ID NO: 4 | 5'-TAATTATAATGGCCGGCTGGGCCTCTAGAGTTACGACGCCAGCGATAACC-3" |
| SEQ ID NO: 5 | 5'-TCTAGAGGCCCAGCCGGCCATTATAATTAG-3' |
| SEQ ID NO: 6 | 5'-GGATCCCATGCTACTCCTACCAACCAAGGT-3' |

Example 2: Production of Aldehyde Dehydrogenase Deletion Vector for Inhibiting 3-HP Biosynthesis When 1,3-PDO is produced from glycerol, 3-HPA, a produced precursor, is converted to 3-HP through the aldehyde dehydrogenase enzyme present in the cell. However, no enzyme that catalyzes the reaction to accept the precursor as a substrate in *Corynebacterium glutamicum* has been reported. Therefore, in order to identify the aldehyde dehydrogenase enzyme that mediates the reaction and delete the gene encoding the enzyme from the genome of the strain to thereby inhibit 3-HP biosynthesis, first, 13 kinds of aldehyde dehydrogenase enzymes present in *Corynebacterium glutamicum* were selected (Table 2).

Then, in order to confirm the inhibitory effect of 3-HP biosynthesis by deletion of the genes (SEQ ID NOS: 56 to 68) encoding the 13 kinds of aldehyde dehydrogenase enzymes, first, the strain including the pTacCC1-HrT vector transformed into *Corynebacterium glutamicum* was produced (Cho et al., *Metabolic Engineering*, 42: 157-167, 2017). Then, i) pCG9ts series each containing sgRNA sequences of 12 types of genes, and ii) ssODNs each binding to 13 kinds of genes for the produced *Corynebacterium glutamicum* strain were produced to perform gene deletion in *Corynebacterium glutamicum*.

2-1: Production of pCG9ts-Series Vectors Containing sgRNA Guide Sequences of 13 Kinds of Genes First, using the online program CRISPy-web (Blin et al., *Synthetic and Systems Biotechnology*, 1(2):118-121, 2016), which analyzes the non-specific target of the guide sequence of sgRNA and provides the optimal sgRNA guide sequence, the following optimal guide sequences having a low off-target effect were selected (Table 2).

TABLE 2 sgRNA guide sequences for 13 arbitrary kinds of aldehyde dehydrogenase using CRISPy-web

| Guide sequence | Target gene | sgRNA guide sequence |
|---|---|---|
| SEQ ID NO: 7 | NCgl0049 | TTCGTGGACTAAGAAACGGT |
| SEQ ID NO: 8 | NCgl0157 | TGCAGGATTGTAGACAGGAG |
| SEQ ID NO: 9 | NCgl0248 | TTCACCTCAGAGACGATTAG |
| SEQ ID NO: 10 | NCgl0437 | TGTTTGCTAAAGAGTAGGAA |
| SEQ ID NO: 11 | NCgl0463 | AACTCCCCGCGAAAGATCCG |
| SEQ ID NO: 12 | NCgl0521 | TTCGGAGACACACACATGTA |
| SEQ ID NO: 13 | NCgl0523 | CCAGTGACTTTAGAGCTAGG |
| SEQ ID NO: 14 | NCgl0900 | CCAACTGATATCGTGCTGTA |
| SEQ ID NO: 15 | NCgl1526 | GTCGCCAGTGTATGCGTGAA |
| SEQ ID NO: 16 | NCgl2272 | GCGCAGCAAAGCTACGTTTC |
| SEQ ID NO: 17 | NCgl2578 | ATCGTCGTAAGGATTGATAT |
| SEQ ID NO: 18 | NCgl2619 | GAGGTTATAGCGCCATTTAC |
| SEQ ID NO: 19 | NCgl2698 | CTTGCCAATCCGATTAGAGC |

In order to produce pCG9ts-series vectors including the sgRNA guide sequences (SEQ ID NOS: 7 to 19), DNA fragments targeting the NCgl0049 gene and encoding the sgRNA-T1/TE sequence (Korea Patent Application No. 2017-0042124; Cho et al., *Metabolic Engineering*, 42: 157-167, 2017) were amplified using pUC19-sgRNA vector (Korean Patent Application No. 2017-0042124; Cho et al., *Metabolic Engineering*, 42: 157-167, 2017, SEQ ID NO: 55) as a template and primers of SEQ ID NOS: 20 and 23. The amplified DNA fragments were amplified again through PCR using the primers of SEQ ID NOS: 21 and 22. After a pEKts-Cas9 vector (Korean Patent Application No. 2017-0042124; Cho et al., *Metabolic Engineering*, 42: 157-167, 2017, SEQ ID NO: 66) was treated with a StuI enzyme, a pCG9ts-ALD1 vector expressing the sgRNA targeting the NCgl0049 gene together with the Cas9 protein was finally produced through Gibson assembly with the amplified fragment. Then, fragments targeting genes encoding each of 13 arbitrary kinds of enzymes were produced in the same manner as above (the same in the case of SEQ ID NOS: 20, 21 and 22; PCR was conducted in the order of SEQ ID NOS: 24 to 35 for respective genes) to produce pCG9ts-ALD2, pCG9ts-ALD3, pCG9ts-ALD4, pCG9ts-ALD5, pCG9ts-ALD6, pCG9ts-ALD7, pCG9ts-ALD8, pCG9ts-ALD9, pCG9ts-ALD10, pCG9ts-ALD11, pCG9ts-ALD12 and pCG9ts-ALD13 vectors.

TABLE 3

Primers for amplifying sgRNA-T1/TE fragments

| SEQ ID NO | Nucleotide sequence |
|---|---|
| SEQ ID NO: 20 | TATAGATATCCCGCGGTATATTAATTAATATAAACGCAGAAAGGCCC |
| SEQ ID NO: 21 | TGGATGATGGGCGATTCAGGtatagatatcTTGACAATTAATCATCGGCT |

TABLE 3-continued

Primers for amplifying sgRNA-T1/TE fragments

| SEQ ID NO | Nucleotide sequence |
|---|---|
| SEQ ID NO: 22 | AAGGTGTTGCTGACTCATACCAGGTATAGATATCCCGCGGTATA |

TABLE 4

Primers for producing pCG9ts-series vectors and 13 randomly selected enzymes

| SEQ ID NO | Gene | Annotation | Nucleotide sequence |
|---|---|---|---|
| SEQ ID NO: 23 | NCgl0049 | SSADH | ttgacaattaatcatcggctcgtataatgtgtggTTCGTGGACTAAGAAACGGTgttttagagctagaaatagcaagt |
| SEQ ID NO: 24 | NCgl0157 | mqo | ttgacaattaatcatcggctcgtataatgtgtggTGCAGGATTGTAGACAGGAGgttttagagctagaaatagcaagt |
| SEQ ID NO: 25 | NCgl0248 | asd | ttgacaattaatcatcggctcgtataatgtgtggTTCACCTCAGAGACGATTAGgttttagagctagaaatagcaagt |
| SEQ ID NO: 26 | NCgl0437 | | ttgacaattaatcatcggctcgtataatgtgtggTGTTTGCTAAAGAGTAGGAAgttttagagctagaaatagcaagt |
| SEQ ID NO: 27 | NCgl0463 | SSADH | ttgacaattaatcatcggctcgtataatgtgtggAACTCCCCGCGAAAGATCCGgttttagagctagaaatagcaagt |
| SEQ ID NO: 28 | NCgl0521 | | ttgacaattaatcatcggctcgtataatgtgtggTTCGGAGACACACACATGTAgttttagagctagaaatagcaagt |
| SEQ ID NO: 29 | NCgl0523 | betB | ttgacaattaatcatcggctcgtataatgtgtggCCAGTGACTTTAGAGCTAGGgttttagagctagaaatagcaagt |
| SEQ ID NO: 30 | NCgl0900 | gapB | ttgacaattaatcatcggctcgtataatgtgtggCCAACTGATATCGTGCTGTAgttttagagctagaaatagcaagt |
| SEQ ID NO: 31 | NCgl1526 | gapA | ttgacaattaatcatcggctcgtataatgtgtggGTCGCCAGTGTATGCGTGAAgttttagagctagaaatagcaagt |
| SEQ ID NO: 32 | NCgl2272 | proA | ttgacaattaatcatcggctcgtataatgtgtggGCGCAGCAAAGCTACGTTTCgttttagagctagaaatagcaagt |
| SEQ ID NO: 33 | NCgl2578 | vdh | ttgacaattaatcatcggctcgtataatgtgtggATCGTCGTAAGGATTGATATgttttagagctagaaatagcaagt |
| SEQ ID NO: 34 | NCgl2619 | gabD2/ssadh | ttgacaattaatcatcggctcgtataatgtgtggGAGGTTATAGCGCCATTTACgttttagagctagaaatagcaagt |
| SEQ ID NO: 35 | NCgl2698 | ald | ttgacaattaatcatcggctcgtataatgtgtggCTTGCCAATCCGATTAGAGCgttttagagctagaaatagcaagt |

2-2: Production of ssODN Each Binding to 13 Types of Genes

SsODN for deleting 13 arbitrary kinds of target genes was designed so that the site where the guide sequence of sgRNA binds was located between the two binding sequences of ssODN, and the total length was 80 nucleotides (Table 5). At this time, ssODN consists of a 5'-homology arm and a 3'-homology arm, and each homology arm is 40 base pairs, and was designed to bind to the outer parts of both ends of the target gene region including a sequence complementary to the guide sequence of sgRNA. When ssODN binds to the target, a loop structure is formed, and this part becomes a region where deletion occurs. The length of the deletion region was designed to have 100 base pairs so that deletion of the target gene could be easily detected through PCR.

TABLE 5

SsODN sequences binding to arbitrary 13 kinds of aldehyde dehydrogenase genes

| SEQ ID NO | Nucleotide sequence |
|---|---|
| SEQ ID NO: 36 | ggtgccatgggtgccaaaatgcgcaacatcggcgaagcttcgacgaaggcgtcaccgtgggcccctggttgaggaaaaa |
| SEQ ID NO: 37 | actggattgacggcgcgatttccccatccacttccggcaagctgctaagacgtggggcaacctgtcatcgctaagcgcc |
| SEQ ID NO: 38 | gactgttgtggataactcttctgcttggcgcaaggacgaccagtgctgaagccacttcacgatgccgctggtcttgtaaa |
| SEQ ID NO: 39 | gtcggtagcatcaaaagctcgcacgccgatgagtggccactcgccatcaatcagtgaacacccatgcagtgcggttg |
| SEQ ID NO: 40 | ccacgattccaccccagtggatgtccgcgctctctgatgcacagagatcatccacctggaagctgaaaaatccgttgcaga |
| SEQ ID NO: 41 | gtaaccaccttgcttcgggtatagaagttgaaagactcaggacttcgatgtccatctgaaattctcgagctgtacggcca |
| SEQ ID NO: 42 | gtcgagagtactgacatgtctgcatcaggaaggataatcgccttgtctactccggggtggcggacaagggcatcaccgaaa |

TABLE 5-continued

SsODN sequences binding to arbitrary 13 kinds of aldehyde dehydrogenase genes

| SEQ ID NO | Nucleotide sequence |
|---|---|
| SEQ ID NO: 43 | cttcgaagaatccgaaagcaccgacctgcgtgc cttcctgtcctggtttcccgcgaggcactgtat gacggtgctcgtct |
| SEQ ID NO: 44 | aacgatgttgactgctgctgcacgtgcacgacg caggtcgttggtgcgaggcagttggtggtgcaa gatgcgccggagat |
| SEQ ID NO: 45 | ctgcaggataccacgagcaggtgaggaatgcac agctcgcccaaaggcacacggacctgcacatct gaatgccgtt |
| SEQ ID NO: 46 | ggcatcaacatcagcaatggaagcagtagcatc ggcgcaaatgagcagtcacaaggtctcctaaag agattgtgg |
| SEQ ID NO: 47 | cccagaaagtgcaaaagcatgctcgacgtcagc tcatcatgaagacataggcagcggacctaaagg aagacgtttg |
| SEQ ID NO: 48 | ggaatgatcttgtcggatgcagcgcggttgatc agcttgcgccctctgggatgagatcgccgatga tgttaatcagatac |

Example 3: Production and Confirmation of *Corynebacterium glutamicum* with Inhibited 3-HP Production Ability and Improved 1,3-PDO Production Ability 3-1: Production of *Corynebacterium glutamicum* with Inhibited 3-HP Production Ability The pCG9ts-ALD vectors and ssODN produced in Examples 2-1 and 2-2 were each transformed into wild-type *Corynebacterium glutamicum* (ATCC 13032) in order to delete the genes encoding arbitrary 13 kinds of aldehyde dehydrogenase that were expected to be involved in 3-HP biosynthesis from the genome. Then, for the transformed mutant *Corynebacterium glutamicum* strains, a pTacCC1-HrT vector (Korean Patent Application No. 2017-0042124; Cho et al., *Metabolic Engineering*, 42: 157-167, 201, SEQ ID NO: 57) and pCG9ts-ALD vectors were removed by curing on a 37° C. BHI plate. The strains produced through this process are shown in Table 6. However, the WAH3 strain and the WAH9 strain were not produced and the corresponding two genes are considered to be genes essential for cell survival.

TABLE 6

11 kinds of arbitrary aldehyde dehydrogenase-deleted *Corynebacterium glutamicum* strains

| Name of strain | Genotype |
|---|---|
| WT | *C. glutamicum* ATCC 13032 |
| WAH1 | WT NCgl0049 |
| WAH2 | WT NCgl0157 |
| WAH4 | WT NCgl0437 |
| WAH5 | WT NCgl0463 |
| WAH6 | WT NCgl0521 |
| WAH7 | WT NCgl0523 |
| WAH8 | WT NCgl0900 |
| WAH10 | WT NCgl2272 |
| WAH11 | WT NCgl2578 |
| WAH12 | WT NCgl2619 |
| WAH13 | WT NCgl2698 |

3-2: Production of pEK-pduyE Vector for Construction of 1,3-PDO Biosynthetic Metabolic Pathway In order to construct the 1,3-PDO biosynthetic metabolic pathway, *Klebsiella pneumoniae* DSMZ2026 (KCTC 4952) and *E. coli* W3110-derived foreign enzymes were expressed using the pEKEx1 shuttle vector of *Corynebacterium glutamicum* (Eikmanns et al., Gene 102: 93, 1991, SEQ ID NO: 58).

First, PCR was performed using the chromosomal DNA of the DSMZ2026 strain of *Klebsiella pneumoniae* as a template and primers of SEQ ID NOS: 49 and 50 to obtain a pduCDEGH gene cluster fragment (SEQ ID NO: 59) encoding glycerol dehydratase and glycerol reactivase. In order to ligate the obtained pduCDEGH gene fragment with the pEKEx1 vector as a shuttle vector, a pEK-pdu vector was produced by treatment with the restriction enzymes EcoRI and PstI, and then ligation using Gibson assembly (FIG. 4).

Then, PCR was performed using the pTac15kyqhD recombinant vector (a recombinant vector (SEQ ID NO: 60) obtained by inserting yqhD derived from *E. coli* W3110 into a pTac15k vector (originated from p15A, tac promoter, KmR), as a template and primers of SEQ ID NOS: 51 and 52 to obtain a yqhD gene fragment encoding 1,3-PDO oxidoreductase.

In order to ligate the obtained gene fragment with the pEK-pdu vector, a pEK-pduyE vector was produced by treatment with the DraI restriction enzyme and ligation using Gibson assembly (FIG. 5).

TABLE 7

Primers for producing pEK-pduyE vectors

| SEQ ID NO | Nucleotide sequence |
|---|---|
| SEQ ID NO: 49 | 5'-ACAATTTCACACAGGAAACAGAATT CATGAGATCGAAAAGATTTGAAG-3' |
| SEQ ID NO: 50 | 5'-AAAACAGCCAAGCTTGGCTGCAGT TAAGCATGGCGATCCCGAAATG-3" |
| SEQ ID NO: 51 | 5'-TTCCAATGATGAGCACTTTT TTGACAATTAAT-3' |
| SEQ ID NO: 52 | 5'-GCGCCACATAGCAGAACTTTTTAG CGGGCGGCTTCGTATATAC-3' |

3-3: Confirmation of Inhibition of 3-HP Production Ability and Improvement of 1,3-PDO Production Ability Through In Vivo Culture Each strain prepared in Example 3-1 was transformed with the pCSglpFKD vector for constructing a glycerol-degrading metabolic pathway and pEK-pduyE for constructing a 1,3-PDO biosynthetic metabolic pathway. Then, selection was conducted on a BHIS plate medium (containing 37 g/L of brain heart infusion (BHI), 91 g/L of sorbitol and 15 g/L of agar) supplemented with 25 µg/L of Kanamycin and 200 µg/L of Spectinomycin. The 11 transformed mutant microorganisms were inoculated into a test tube containing 10 mL BHIS medium (containing 37 g/L of brain heart infusion (BHI) and 91 g/L of sorbitol) and pre-cultured at 30° C. for 16 hours. Then, 1 mL of the pre-cultured solution was inoculated into 25 mL of CGXII medium (Table 8) in a 250 mL baffle flask and cultured. The initial glycerol concentration was set to 40 g/L, and g/L of yeast extract in the medium was added, and flask culture was performed in triplicate for 48 hours.

TABLE 8

Components of CGXII medium used for culture of *Corynebacterium glutamicum*

| Components of CGXII-glycerol medium | Concentration |
|---|---|
| $CaCl_2 \cdot 2H_2O$ | 13 mg/L |
| $FeSO_4 \cdot 7H_2O$ | 10 mg/L |
| $MnSO_4 \cdot 5H_2O$ | 14 mg/L |
| $ZnSO_4 \cdot 7H_2O$ | 1 mg/L |
| $CuSO_4 \cdot 5H_2O$ | 300 µg/L |
| $NiCl_2 \cdot 6H_2O$ | 20 µg/L |
| $(NH_4)_2SO_4$ | 20 g/L |
| Urea | 2 g/L |
| $KH_2PO_4$ | 1 g/L |
| $K_2HPO_4$ | 1 g/L |
| Biotin | 200 µg/L |
| Thiamine | 500 µg/L |
| Protocatechuic acid | 30 mg/L |
| MOPS | 42 g/L |
| Glycerol | 40 g/L |
| Spectinomycin | 200 µg/L |

The HPLC conditions used to measure the 3-HP concentration are as follows. First, an Agilent 1100 series HPLC instrument was used, and a DAD detector, an agilent Meta-Carb 87H column, and another UV 210 nm detector were used as detectors and a column. At this time, 0.1% H3PO4 was fed as a buffer at a flow rate of 0.5 mL/min at 40° C. Next, Waters 1515 high performance liquid chromatography (Waters 1 Co., Milford, Mass., USA) was used for the measurement of 1,3-PDO. The detectors and column used herein were Waters 2414 refractive index detectors and A MetaCarb 87H column (300 by 7.8 mm; Agilent). At this time, 0.01N H2504 was fed as a buffer at a flow rate of 0.5 mL/min at 35° C.

As a result, as can be seen from FIGS. 6 and 7, the strain transformed with the pCSglpFKD vector and the pEK-pduyE vector from the WAH13 strain the most inhibited 3-HP production and thus the most increased 1,3-PDO production. In addition, it can be seen that WAH1, WAH2, WAH5, WAH6 and WAH7 also exhibited inhibited 3-HP production and increased 1,3-PDO production.

INDUSTRIAL APPLICABILITY

The mutant *Corynebacterium glutamicum* according to the present invention can produce 1,3-PDO with high efficiency using inexpensive glycerol as a carbon source through inhibition of the ability to produce 3-HP, a by-product.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

[Sequence Text]
An electronic file was attached.

---

The invention claimed is:

1. A mutant *Corynebacterium glutamicum* cell that has been genetically modified by (i) introducing the *E. coli* glpF gene, the *E. coli* glpK gene, the *E. coli* glpD gene, the *E. coli* yqhD gene, and the *K. pneumoniae* pduCDEG operon, and (ii) disrupting an endogenous gene encoding an aldehyde dehydrogenase that comprises comprising a nucleotide sequence selected from the group consisting of SEQ ID NO: 56, 57, 59, 60, 61, 62, 63, 65, 66, 67, and 68.

2. The mutant *Corynebacterium glutamicum* cell according to claim 1, wherein said genes comprise a strong promoter selected from the group consisting of tac, trc and tuf.

3. A method of producing 1,3-propanediol (1,3-PDO) from glycerol comprising:

(a) culturing the mutant *Corynebacterium glutamicum* cell according to claim 1 in a glycerol-containing medium to produce 1,3-PDO; and (b) collecting the produced 1,3-PDO.

* * * * *

UNITED STATES PATENT AND TRADEMARK OFFICE
CERTIFICATE OF CORRECTION

PATENT NO. : 11,473,111 B2
APPLICATION NO. : 17/055971
DATED : October 18, 2022
INVENTOR(S) : Sang Yup Lee et al.

It is certified that error appears in the above-identified patent and that said Letters Patent is hereby corrected as shown below:

In the Specification

Column 6, Line 12, "DH5a" should be -- DH5α --.

Column 8, Line 56, "3 and to" should be -- 3 and 4 to --.

Column 14, Line 65, "and g/L" should be -- and 10 g/L --.

Column 16, Line 3, "H25O4" should be -- $H_2SO_4$ --.

In the Claims

Column 63, Line 15, "comprises comprising" should be -- comprises --.

Signed and Sealed this
Twentieth Day of December, 2022

Katherine Kelly Vidal
*Director of the United States Patent and Trademark Office*